(12) United States Patent
Koppel

(10) Patent No.: US 6,610,681 B1
(45) Date of Patent: Aug. 26, 2003

(54) NEUROTHERAPEUTIC CLAVULANATE COMPOSITION AND METHOD

(75) Inventor: Gary A. Koppel, Indianapolis, IN (US)

(73) Assignee: Revaax Pharmaceuticals, LLC, Indianapolis, IN (US)

(*) Notice: Subject to any disclaimer, the term of this patent is extended or adjusted under 35 U.S.C. 154(b) by 0 days.

(21) Appl. No.: 09/640,362

(22) Filed: Aug. 16, 2000

Related U.S. Application Data

(60) Provisional application No. 60/194,534, filed on Apr. 4, 2000, provisional application No. 60/176,570, filed on Jan. 18, 2000, provisional application No. 60/172,452, filed on Dec. 17, 1999, and provisional application No. 60/149,115, filed on Aug. 16, 1999.

(51) Int. Cl.⁷ .......................................... A61K 31/424
(52) U.S. Cl. ........................................ 514/210.06
(58) Field of Search ................................ 519/210.06

(56) References Cited

U.S. PATENT DOCUMENTS

| | | | |
|---|---|---|---|
| 4,268,503 A | 5/1981 | Imanaka et al. | 424/114 |
| 4,302,447 A | 11/1981 | Horrobin | 424/642 |
| 4,594,247 A | 6/1986 | Brier | 424/114 |
| 5,698,221 A * | 12/1997 | Patel et al. | 424/464 |
| 5,763,603 A | 6/1998 | Trickes | 540/310 |
| 5,795,877 A | 8/1998 | Jackson et al. | 514/75 |
| 5,824,662 A | 10/1998 | Slusher et al. | 514/75 |
| 5,827,537 A * | 10/1998 | Palepu et al. | 424/472 |
| 5,863,536 A | 1/1999 | Jackson et al. | 424/130.1 |
| 5,880,112 A | 3/1999 | Jackson et al. | 514/121 |
| 5,905,076 A | 5/1999 | Singh et al. | 514/210 |
| 5,912,242 A | 6/1999 | Pevarello et al. | 514/210 |
| 5,968,915 A | 10/1999 | Jackson et al. | 514/89 |
| 5,977,090 A | 11/1999 | Slusher et al. | 514/143 |
| 6,004,946 A | 12/1999 | Slusher et al. | 514/75 |
| 6,015,809 A | 1/2000 | Zhu et al. | 514/210 |
| 6,017,903 A | 1/2000 | Slusher et al. | 514/75 |
| 6,204,260 B1 | 3/2001 | Bruns, Jr. et al. | 514/210.1 |
| 2002/0002159 A1 | 1/2002 | Koppel | 514/210.09 |
| 2002/0013270 A1 * | 1/2002 | Bolte | 514/8 |
| 2002/0028761 A1 | 3/2002 | Koppel et al. | 514/1 |
| 2002/0049187 A1 | 4/2002 | Bruns, Jr. et al. | 514/151 |
| 2002/0183304 A1 * | 12/2002 | Koppel | 514/210.1 |

FOREIGN PATENT DOCUMENTS

| | | |
|---|---|---|
| GB | 1 508 977 | 4/1978 |
| WO | WO 95/20980 | 8/1995 |
| WO | WO 97/10247 | 3/1997 |
| WO | WO 97/35839 | 10/1997 |
| WO | WO 98/32766 | 7/1998 |
| WO | WO 99/36403 | 7/1999 |
| WO | WO 00/62067 | 10/2000 |

OTHER PUBLICATIONS

"The Relation Between Fear Induced by Novel Stimulation and Exploratory Behavior" by K. C. Montogomery, J. Comp. Physiol. Psychol. (1955) vol. 48, 254–260.

"Action of Penicillin on Inhibitory Processes in the Cat's Cortex" by H.V. Duijn, P.A. Schwartzkroin, and D.A. Prince, Brain Res. (1973) vol. 53, 470–476.

"Convulsant Actions of Penicillin: Effects on Inhibitory Mechanisms" by H. Meyer and D. Prince (1973) vol. 53, 477–482. Brain Research.

(List continued on next page.)

Primary Examiner—Jeffrey E. Russel
(74) Attorney, Agent, or Firm—Barnes & Thornburg

(57) ABSTRACT

Administration of clavulanic acid and related compounds at low dosages provides significant neurotropic effects in warm-blooded vertebrates evidenced *inter alia* by anxiolytic and anti-aggressive behavior and enhanced cognition believed to be mediated by inhibition of neurogenic enzyme activity. Therapeutic methods for using such compounds and their pharmaceutical formulations are described.

12 Claims, 13 Drawing Sheets

OTHER PUBLICATIONS

"Penicillin Decreases Chloride Conductance in Crustacean Muscle: A Model for the Epileptic Neuron" by B. Hochner, M.E. Spira, and R. Werman, Brain Res. (1976) vol. 107, 85–103.

A.B. Chernomordik, Klin. Med. (1980) vol. 2, 102–105.

"Antagonism by Penicillin of Gamma–Aminobutyric Acid Depolarizations at Presynaptic Sites in Rat Olfactory Cortex and Cuneate Nucleus In Vitro" by H.G. Pickles and M.A. Simmonds, Neuropharmacology (1980) vol. 19, 35–38.

"GABA and the Behavioral Effects of Anxiolytic Drugs" by D.J. Sanger, Life Sciences (1985) vol. 36, 1503–1513.

"Convulsant Doses of Penicillin Shorten the Lifetime of GABA–Induced Channels in Cultured Central Neurones" by P. Chow and D. Mathers, Br. J. Pharmac. (1986) vol. 88, 541–547.

"N–methyl–D–aspartate Receptors and the Enhancement of Somatosensory Evoked Potentials in Penicillin Epileptogenesis in Rats" by Z.I. Bashir and O. Holmes, Physiological Society (1987) 19P.

"Competitive Inhibition of N–Acetylated–alpha–Linked Acidic Dipeptidase Activity by N–Acetyl–L–Aspartyl–beta–Linked L–Glutamate" by V. Serval, L. Barbeito, A. Pittaluga, A. Cheramy, S. Lavielle, and J. Glowinski, J. Neurochemistry (1990) vol. 55, 39–46.

"Time Course of Interictal EEG Patterns Induced by a Penicillin Injection into Olfactory Cortex" by E. Horn, K. Esseling, and R. Wagner, Pharmacology Biochemistry & Behavior (1991) vol. 40, 351–357.

"The Pharmacology of Recombinant $GABA_A$ Receptors Containing Bovine alpha 1, beta 1, gamma2L Sub–units Stably Transfected into Mouse Fibroblast L–Cells" by A.L. Horne, K.L. Hadingham, A.J. Macaulay, P. Whiting, and J.A. Kemp, Br. J. Pharmacology (1992) vol. 107, 732–737.

I.V. Batueva, N.P. Veselkin, and R. Veskov, Neirofiziologiya (1992) vol. 24 (2), 151–160.

"Increased Intra– and Extracellular Concentrations of Gamma–Glutamylglutamate and Related Dipeptides in the Ischemic Rat Striatum: Involvement of Gamma–Glutamly Transpeptidase" by O. Orwar, X. Li, P. Andiné, C.–M. Bergström, H. Hagberg, S. Folestad, and M. Sandberg, J. Neurochemistry (1994) vol. 63, 1371–1376.

"Endogenous Gamma–L–Glutamyl and Beta–L–Aspartyl Peptides and Excitatory Aminoacidergic Neurotransmission in the Brain" by V. Varga, R. Janaky, P. Saransaari, and S.S. Oja, Neuropeptides (1994) vol. 27, 19–26.

"Penicillins and Their Derivatives: Antiucler/Antistress Properties?" by A.V. Kalueff, G.E. Samonina, and I.P. Ashmarin, Neuropschychopharmacology (1994) vol. 10, 272S.

"Behavioral Effects of Penicillin in a Test for Anxiety in Rats" by A.V. Kaluev, G.E. Samonina, and I.P. Ashmarin, Bulletin of Experimental Biology and Medicine (1995) vol. 120, 984–986.

"Design, Synthesis, and Biological Activity of a Potent Inhibitor of the Neuropeptidase N–Acetylated Alpha–Linked Acidic Dipeptidase" by P.F. Jackson, D.C. Cole, B.S. Slusher, S. Stez, L.E. Ross, B.A. Donzanti, and D.A. Trainor, J. Med. Chem. (1996) vol. 39(2), 619–622.

"Gamma–L–Glutamyl–L–Aspartate Induces Specific Deficits in Long–Term Memory and Inhibits [$^3$H]Glutamate Binding on Hippocampal Membranes" by A. Ungerer, M.S. Bourgeois, C. Mélan, Y. Boulanger, J. Reinbolt, I. Amiri, and J.D. Barry, Brain Res. (1988) vol. 446, 205–211.

E.F. Reynolds, "Martindale, The Extra Pharmocopoeia," Royal Pharmaceutical Society, London, p. 211, col. 2–3, (1996) XP–002161510.

Passani, Lucius A., et al., "N–acetylaspartylglutamate, N–acetylaspartate, and N–acetylated alpha–linked acidic dipeptidase in human brain and the alterations in Huntington and Alzheimer diseases," Molecular and Chemical Neuropathology, vol. 31, No. 2, pp. 97–118, (1997) XP–000987254.

Macknin, M.L., "Behavioral changes after amoxicillin–clavulanate," letter, Pediatric Infectious Disease Journal, vol. 6, No. 9, (Sep. 1987) XP–000987254.

Tsai, Guochuan, et al., "Abnormal Excitatory Neurotransmitter Metabolism in Schizophrenic Brains", Archives of General Psychiatry, vol. 52, No. 10, pp. 829–636, (1995) XP–00987256.

Pangalos, Menelas N., et al. "Isolation and expression of novel human glutamate carboxypeptidases with N–acetylated alpha–linked acidic dipeptidase and dipeptidyl peptidase IV activity", Journal of Biological Chemistry, vol. 274, No. 13, pp. 8470–8483 (Mar. 26, 1999), XP–002161509.

Drummond, J. et al., "Synthesis of a Cognition Enhancing Beta–Lactam Fused Gamma–Lactam", Terahedron Ltrs, 28(44):5245–8, (1987).

Kabanov, A. et al., "The neuroleptic activity of halperidol increases after its solubilization in surfactant micelles", FEBS Letters, (1989).

Nilsson, B. et al., "β–Lactam Analogues of Oxotremorine 3– and 4–Methyl–Substituted 2–Azetidinones", J. Med. Chem., 33:580–4, (1990).

* cited by examiner ns known to be required for clinically effective bacterial peptidase inhibition. Thus they can also be used effectively for treating prostate disease and the disease states associated with nervous tissue insult previously described as responsive to treatment with NAALADase inhibitors.

SEQUENCE LISTING

```
<160> NUMBER OF SEQ ID NOS: 6

<210> SEQ ID NO 1
<211> LENGTH: 4
<212> TYPE: PRT
<213> ORGANISM: Homo sapiens

<400> SEQUENCE: 1

Ser Thr Thr Lys
1

<210> SEQ ID NO 2
<211> LENGTH: 4
<212> TYPE: PRT
<213> ORGANISM: Homo sapiens

<400> SEQUENCE: 2

Glu Asn Lys Asp
1

<210> SEQ ID NO 3
<211> LENGTH: 4
<212> TYPE: PRT
<213> ORGANISM: Homo sapiens

<400> SEQUENCE: 3

Ser Thr Gln Lys
1

<210> SEQ ID NO 4
<211> LENGTH: 4
<212> TYPE: PRT
<213> ORGANISM: Homo sapiens

<400> SEQUENCE: 4

Glu Arg Gly Val
1

<210> SEQ ID NO 5
<211> LENGTH: 4
<212> TYPE: PRT
<213> ORGANISM: Homo sapiens

<400> SEQUENCE: 5

Asn Ser Arg Lys
1
```

-continued

```
<210> SEQ ID NO 6
<211> LENGTH: 4
<212> TYPE: PRT
<213> ORGANISM: Homo sapiens

<400> SEQUENCE: 6

Glu Arg Ser Ile
1
```

NEUROTHERAPEUTIC CLAVULANATE COMPOSITION AND METHOD

CROSS-REFERENCE TO RELATED APPLICATION

This application claims priority to U.S. Provisional Serial Nos. 60/149,115, filed Aug. 16, 1999; Ser. No. 60/172,452, filed Dec. 17, 1999; Ser. No. 60/176,570, filed Jan. 18, 2000, and U.S. Provisional Application Serial No. 60/194,534, filed Apr. 4, 2000.

FIELD OF INVENTION

This invention relates to a novel mechanism of neuropsychiatric intervention. More particularly, this invention is directed to pharmaceutical formulations and methods for treatment of a variety of peptidase mediated disease states, including cognitive and behavioral disorders.

BACKGROUND AND SUMMARY OF THE INVENTION

The pharmaceutical industry has directed extensive research and development efforts toward discovery and commercialization of drugs for treatment of neurological disorders. Such disorders typically derive from chemical imbalances in the brain. Overproduction or underproduction of pertinent neurochemical species and/or receptor dysfunction has been identified with many disease states recognized by neurologists, psychiatrists, psychologists and other medical practitioners skilled in the diagnosis and treatment of mental disease. Most of the discovery effort for new neurologically active drugs has been based on the study of agonist/antagonist drug interaction with one or more of the numerous receptors in the brain and/or their respective receptor ligands.

The present invention provides a novel approach to drug intervention in the treatment of a wide variety of neurologic disease states and other disease states or clinical conditions of related etiology. It is based in part on the discovery that β-lactam containing compounds known for their activity as inhibitors of bacterial peptidases or proteases, particularly transpeptidases and/or carboxypeptidases, are also potent inhibitors of certain mammalian peptidases generically referred to as N-acetylated-α-linked acidic peptidases (NAALADases), several of which have been identified/characterized in the literature [Pangalos et al., *J. Biol. Chem.*, 1999, 274, No. 13, 8470–8783]. The present invention is also based in part on the discovery that neurogenic NAALADases can be targeted with NAALADase inhibitors to effect significant behavioral modification and enhanced cognitive performance. Preliminary studies have confirmed that one or more neurogenic proteases, now believed to be NAALADases, capable of recognizing and transforming certain neuropeptides (e.g., N-acetyl-L-aspartyl-L-glutamate) play a significant if not dominant role at the neurochemical level of brain function and concomitantly have a substantial impact on patient behavior and cognitive performance. It has been previously reported that certain glutamate analogs acting as NAALADase inhibitors can be used to treat prostate disease and glutamate abnormalities associated with certain nervous tissue insult. It has now been determined that NAALADase inhibitors, including particularly certain bacterial peptidase and β-lactamase inhibitors capable of blood-brain barrier transport, can function in the brain at very low concentrations as potent neuroactive drug substances to reduce the symptoms of a wide variety of neurological disorders characterized by behavioral aberration or cognitive dysfunction. Significantly such bacterial enzyme inhibitors are believed to be effective NAALADase inhibitors at concentrations below those concentrations known to be required for clinically effective bacterial peptidase inhibition. Thus they can also be used effectively for treating prostate disease and the disease states associated with nervous tissue insult previously described as responsive to treatment with NAALADase inhibitors.

Accordingly, one embodiment of the present invention is directed to a method for treatment of cognitive and behavioral disorders in warm-blooded vertebrates by administering compounds known for their activity as bacterial protease or peptidase inhibitors, which compounds, when present at effective concentrations in the brain, have now been determined to be capable of inhibiting or otherwise modulating the activity of one or more neurogenic NAALADases.

In a related embodiment there is provided method for treatment of cognitive and behavioral disorders in a patient in need of such treatment. The method comprises the step of inhibiting neurogenic NAALADase activity. In one embodiment such neuropeptidase inhibition is effected by administering an effective amount of a β-lactam compound recognized for its capacity to bind to and inhibit a bacterial enzyme, for example, a β-lactamase or a bacterial protease involved in bacterial cell wall synthesis and exhibiting selective proteolytic activity on bacterial peptidoglycans. Such bacterial proteases are known in the art as "penicillin binding proteins." In another embodiment of the present invention, the method is effected by administration of art-recognized NAALADase inhibitors, including particularly certain deaminoglutamate analogues and N-substituted glutamate derivatives. Effective inhibition of such neuropeptidase activity in warm-blooded vertebrates has been found to produce marked enhancement in cognitive performance and behavioral management.

Exemplary of cognitive and behavioral disorders susceptible to treatment in accordance with this invention include aggressive disorder, obsessive compulsive disorder, anxiety, depression, ADHD, and memory impairment. Animal data suggest that the method and formulation of this invention have potential as an antiaggressive agent to control impulsivity and violence in autism, Tourette's syndrome, mental retardation, psychosis, mania, senile dementia and individuals with personality disorders and history of inappropriate aggression. Clinic applications extend to the treatment of children with ADHD and conduct disorder, as an anxiolytic, and as a cognition enhancer for the geriatric population to improve learning and memory and to ameliorate disorientation.

In another embodiment of this invention there is provided a method of treating a patient afflicted with a condition, or disposed to development of a condition, characterized at least in part by abnormal extracellular concentration of glutamate in the brain or other nervous tissue. The method comprises the step of administering to the patient in effective amounts of a compound capable of inhibiting the activity of a penicillin-binding protein of bacterial origin. The composition is administered in an amount effective to prevent or alleviate the symptoms of such condition. Thus, for example, localized high glutamate concentrations in the brain have been reported in stroke victims and victims of other brain trauma. More recently high glutamate concentrations in the brain and peripheral nerve tissue have been reported to be associated with multiple sclerosis.

In still another embodiment of the invention there is provided a method for treating prostate disease selected from prostate cancer and benign prostate hyperplasia in a human patient. The method comprises the step of administering to the patient a composition comprising a compound capable of inhibiting the activity of a penicillin-binding protein of bacterial origin. The compound is administered in an amount effective to retard the progress of the disease or to reduce the symptoms of the disease.

One group of compounds for use in accordance with this invention are β-lactam compounds, i.e., compounds having a β-lactam ring system, including particularly β-lactam antibiotics such as penicillins, cephalosporins and analogues thereof. In one preferred embodiment the β-lactam compound is clavulanic acid and pharmaceutically acceptable derivatives thereof. Further, the peptide Ala-D-γ-Glu-Lys-D-Ala-D-Ala (believed to serve as a substrate for NAALADase) has been found effective as a peptidase inhibitor useful for behavior modification and cognitive/sensory enhancement in accordance with the invention. Non-β-lactam NAALADase inhibitors have been reported in the patent and non-patent literature. See, e.g., U.S. Pat. Nos. 5,795,877; 5,804,602; 5,968,915; 5,902,817; 5,962,521 and 5,863,536, the specifications of which are specifically incorporated herein by reference for their teaching of such NAALADase inhibitors and the use generally of such NAALADase inhibitors for treatment of certain disease states responsive to NAALADase inhibition therapy. Other compounds capable of use in accordance with this invention can be identified using molecular modeling studies. The antibiotic compounds for use in this invention can be administered in combination with one or more of other enzyme inhibitors, for example, effective amounts of a β-lactamase inhibitor (where the active compound is a β-lactam) or another NAALADase inhibitor or a P-glycoprotein efflux inhibitor to enhance brain levels of the active compound. The method and formulation embodiments of the invention find use in both human health and veterinary applications, e.g., in canine, feline and equine species.

In one embodiment a warm-blooded vertebrate, most typically a human patient, affected by a neurologic disease state characterized by cognitive or behavioral abnormalities is treated with a 1-oxa-1-dethia cephalosporin, more preferably a 7-methoxy-1-oxa-1-dethia cephalosporin, optionally as an active ester derivative in an orally (including buccal or sublingual administration) or a parenterally administered formulation. In one embodiment, the peptidase inhibitor is moxalactam, [7-β-[2-carboxy-2-(4-hydroxyphenyl)acetamido]-7α-methoxy-3-[[(1-methyl-1H-tetrazol-5-yl)thio]methyl]-1-oxa-1-dethia-3-cephem-4-carboxylic acid], described and claimed with related compounds, including their orally absorbed active ester derivatives, in U.S. Pat. No. 4,323,567, the specification of which is expressly incorporated herein by reference. Moxalactam has been found to exhibit significant dose responsive neuroactivity when administered parenterally at least at about 50 μg/kg of body weight. Clavulanic acid has also been found to exhibit dose responsive neuroactivity when administered at levels as low as 10 ng/kg.

In another embodiment of the present invention there is provided a pharmaceutical formulation for treatment with consequent reduction of symptoms of behavioral or cognitive disorders in patients in need of such treatment. The formulation comprises a compound characterized by its affinity to bacteria derived penicillin-binding proteins. In one embodiment the compound is capable of binding to and inhibiting the function of a bacterial protease known to exhibit its proteolytic activity on a peptidoglycan substrate comprising the C-terminal peptide sequence acyl-D-alanyl-D-alanine. In one preferred embodiment the compound is capable of binding to β-lactamase, another bacterial protein capable of binding to penicillin, and inhibiting the function of that enzyme. The amount of the inhibitor used in the formulation is that determined to be effective to inhibit the activity of endogenous NAALADase. In one embodiment the amount is effective to inhibit NAALADase in the brain at a level sufficient to modulate cognitive and behavioral characteristics. In that later embodiment the level of activity exhibited by the NAALADase inhibitor in the present method is not only dependent on its affinity to penicillin-binding proteins and to NAALADase, it is also particularly dependent on ability of the inhibitor compound to cross the blood brain barrier to achieve levels in the brain effective to modify patient behavior and/or cognitive performance. Clavulanic acid and formulations thereof have been found to exhibit the most robust neurologic activity, presumptively due to its high bioavailability, its good blood brain transport, and its apparent high affinity to NAALADase and probably other structurally related neurogenic peptidases.

In one embodiment of the invention the pharmaceutical formulation comprises a β-lactam containing compound selected from the group consisting of penicillin, cephalosporins, β-lactam containing analogues thereof, including β-lactamase inhibitors, and a pharmaceutical carrier for such β-lactam containing compound. In cases where the β-lactam compound is, for example, a commercially available antibiotic, the amount of β-lactam compound in said formulation is less than that required to produce, upon administration by the commercially detailed mode of β-lactamase inhibitors, and a pharmaceutical carrier for such β-lactam containing compound. In cases where the β-lactam compound is, for example, a commercially available antibiotic, the amount of β-lactam compound in said formulation is less than that required to produce, upon administration by the commercially detailed mode of administration, clinically effective antibiotic blood levels of the compound. Yet the reduced dosage levels of said antibiotics can be effective, assuming reasonable blood-brain barrier transport properties, to produce brain and CSF levels of the compound sufficient to inhibit neurogenic protease (NAALADase) activity in the brain and modify cognitive and behavioral characteristics. Such formulations can optionally include, in addition, effective amounts of one or more of a β-lactamase inhibitor and a P-glycoprotein efflux pump inhibitor or another compound capable of inhibiting the activity of NAALADase and related neurogenic enzymes. In one preferred embodiment the formulation comprises clavulanic acid or a pharmaceutically acceptable salt or active ester form thereof, and a pharmaceutically acceptable carrier wherein the formulation is free of any clinically effective β-lactam antibiotic. While the formulations of this invention can be prepared specifically for any art-recognized mode of administration capable of achieving threshold minimum protease inhibiting concentrations in the brain, they are typically formulated for parenteral or oral administration, optionally in the form of prolonged release or "drug depot" type formulations well known in the art.

DETAILED DESCRIPTION OF THE INVENTION

Figure 1:
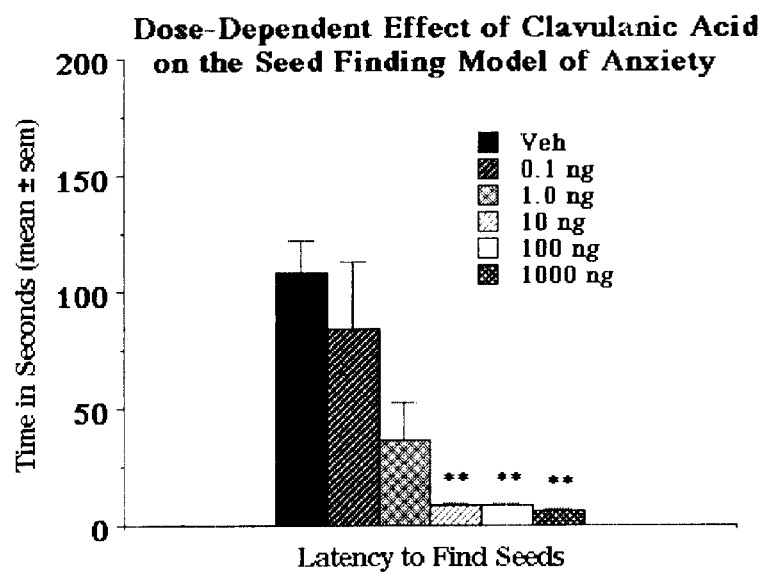
FIGS. 1–18 are graphic representations of data gathered in the conduct of testing of clavulanic acid and other compounds in various animal models accepted in the art for detection of activity against offensive aggression (FIGS. 14, 15, 17 and 18), general motor activity (FIG. 3), anxiolytic activity (FIGS. 1, 2, 4, 13 and 16), and spatial memory (FIGS. 5–12).

The present invention and the various embodiments described and claimed herein derive, in part, from the discoveries that compounds capable of binding to and inhibiting enzyme activity of penicillin-binding proteins of bacterial same in the brain, NAALADase inhibitors exhibit clinically significant neuroactivity evidenced in part by behavioral modification and enhanced cognition function.

In one embodiment the NAALADase inhibitors effective for use in accordance with the present invention are characterized by their capacity to inhibit a bacterial protease exhibiting selective proteolytic activity on a protein or peptide substrate comprising acyl-D-alanyl-D-alanine. Alternatively stated, effective NAALADase inhibitors for use in treatment of behavioral and cognitive disorders in accordance with one embodiment of this invention, can be characterized by their selective affinity (by associative and/or covalent binding) to penicillin-binding proteins; such compounds include particularly β-lactam antibiotics such as penicillins, cephalosporins and analogues thereof. Based on animal tests to date, such bacterial protease inhibitors appear to function at subclinical-antibiotic levels in the brain to inhibit neuropeptidase activity which has a critical function in neurochemical mediation of behavior and cognitive performance. In accordance with the presently claimed invention effective inhibition of neuropeptidase activity with concomitant mediation of behavior and cognitive performance has been effected by administration of a β-lactamase inhibitor, clavulanic acid, a β-lactam containing compound having no clinically significant antibiotic activity. It is surmised that inhibition of such neuropeptidase (e.g., NAALADase) activity allows modulation of the concentration and/or function of one or more neurotransmitters or neuromodulators with concomitant improvement in neurological function evidenced by enhancement of cognitive performance and attenuation of aberrant behavioral phenotypes. Moxalactam given i.p. at 50 micrograms/kg inhibits aggression in hamster, enhances spatial learning in rats, and acts as an anxiolytic in rats. Clavulanic acid has shown similar activity when administered i.p. at less than 1 microgram/kg.

Historically, those knowledgeable in the field of beta lactam antibiotics understand that the mode of action as antibacterial agents is by inhibiting cell wall synthesis by acting as a substrate for penicillin-binding protein (PBP); the term PBP has been extended to include binding to all beta lactams including cephalosporins. More recently, investigators have been able to clone and sequence these PBP's as well as crystallize the enzymes and determine active site motifs (see P. Palomeque et al., *J. Biochem.*, 279, 223–230, 1991). Based on this data, the four putative binding sites for PBP have been designated active site I, II, III and IV. The active sites, sequence location and amino acid (AA) sequence are as follows:

Active site I:
35 AA's downstream from N-terminus: STTK (SEQ ID NO:1)
Active site II:
57 AA's downstream from STTK (SEQ ID NO:1) motif: SGC, SGN, or SAN
Active site III:
111 AA's downstream from SGC motif: KTG
Active site IV:
41 AA's downstream from SGC motif: ENKD (SEQ ID NO:2)

Pursuant to identifying an enzyme system in the brain that moxalactam would inhibit in a similar manner to PBP, it was discovered that a glutamyl carboxypeptidase enzyme known as N-acetyl-α-linked acidic dipeptidase (NAALADase) (See M. N. Pangalos et al., *J. Bio. Chem.*, 264, 8470–8483, 1999) has an almost perfect overlap of the putative active sites of PBP. This enzyme system is responsible for regulating the glutamatergic neurotransmission pathways, the effects of which would be expressed in such behavioral outcomes as aggression, memory/cognition, and anxiety. As a result of the almost perfect overlap of the putative active sites of PBP and the conserved sequences in human and rat NAALADase, it is believed that moxalactam and other β-lactam compounds mediate behavioral effects by inhibiting NAALADase at low concentrations. This is based on the following overlap sequence similarity between PBP and NAALADase I, one of several known NAALADase species, as shown below:

Active site I:
PBP: 35 AA's downstream from N-terminus: STTK (SEQ ID NO:1)
NAALADase: 38 AA's downstream from N-terminus: STQK (SEQ ID NO:3)
Active site II:
PBP: 57 AA's downstream from STTK (SEQ ID NO:1) motif: SGC, SGN, or SAN
NAALADase: 59 AA's downstream from STQK (SEQ ID NO:3) motif: SFG
Active site III:
PBP: 111 AA's downstream from SGC motif: KTG
NAALADase: 110 AA's downstream from SFG motif: KLG
Active site IV:
PBP: 41 AA's downstream from SGC motif: ENKD (SEQ ID NO:2)
NAALADase: 41 AA's downstream from SFG motif: ERGV (SEQ ID NO:4)

Since the beta-lactams provide their inhibition of PBP transpeptidation of bacterial cell wall by binding to these four active sites, one can infer that the conserved similarity in active site sequences and location would confer similar binding properties of moxalactam and other β-lactam compounds to NAALADase. That discovery coupled with observation of the significant behavioral modification effects deriving from administration of very low doses of certain penicillin protein binding compounds has provided insight into a novel approach to the prevention and treatment of disease states characterized by neurological dysfunction.

The unique neurological activity profiles of the two β-lactam compounds that have been studied most extensively to date, moxalactam and clavulanic acid, suggest that those compounds exhibit activity on multiple neurogenic enzyme targets, including NAALADase and structurally related enzymes, particularly those that might share the four active binding site motif common to both PBP and NAALADase. To identify other putative neurogenic targets for the behavioral and cognitive activities discovered for moxalactam and clavulanic acid, the sequence for NAALADase II was used to search the human genome database (NCBI-BLAST). Seven human gene sequences were identified that have significant homology with NAALADase II and that encode for the four active site motif:

1) >dbj/AP001769.2/AP001769 Homo sapiens chromosome 11 clone RP11-240F8 map 11g14
Active site I:
PBP: 35 AA's downstream from N-terminus: . . . STTK (SEQ ID NO:1)
NAALADase: 38 AA's downstream from N-terminus: STQK (SEQ ID NO:3)

>dbj/AP001769: NSRK (SEQ ID NO:5)
Active site II:
PBP: 57 AA's downstream from STTK (SEQ ID NO:1) motif: . . . SGC, SGN, or SAN
NAALADase: 59 AA's downstream from STQK (SEQ ID NO:3) motif: SFG
>dbj/AP001769: SFG
Active site III:
PBP: 111 AA's downstream from SGC motif: . . . KTG
NAALADase: 110 AA's downstream from SFG motif: KLG
>dbj/AP001769: KLG
Active site IV:
PBP:41 AA's downstream from SGC motif: . . . ENKD (SEQ ID NO:2)
NAALADase: 41 AA's downstream from SFG motif: ERGV (SEQ ID NO:4)
>dbj/AP001769: ERSI (SEQ ID NO:6)

2) >dbj|AP000827.2|AP000827 Homo sapiens chromosome 11 clone RP.
Active site I:
PBP: 35 AA's downstream from N-terminus: . . . STTK (SEQ ID NO:1)
NAALADase: 38 AA's downstream from N-terminus: STQK (SEQ ID NO:3)
>dbj|AP000827.2: NSRK (SEQ ID NO:5)
Active site II:
PBP: 57 AA's downstream from STTK (SEQ ID NO:1) motif: . . . SGC, SGN, or SAN
NAALADase: 59 AA's downstream from STQK (SEQ ID NO:3) motif: SFG
>dbj|AP000827.2: SFG
Active site III:
PBP: 111 AA's downstream from SGC motif: . . . KTG
NAALADase: 110 AA's downstream from SFG motif: KLG
>dbj|AP000827.2: KLG
Active site IV:
PBP:41 AA's downstream from SGC motif . . . ENKD (SEQ ID NO:2)
NAALADase: 41 AA's downstream from SFG motif: ERGV (SEQ ID NO:4)
>dbj|AP000827.2: ERSI (SEQ ID NO:6)

3) >dbj|AP000648.2|AP000648 Homo sapiens chromosome 11 clone CM.
Active site I:
PBP: 35 AA's downstream from N-terminus: . . . STTK (SEQ ID NO:1)
NAALADase: 38 AA's downstream from N-terminus: STQK (SEQ ID NO:3)
>>dbj|AP000648.2: NSRK (SEQ ID NO:5)
Active site II:
PBP: 57 AA's downstream from STTK (SEQ ID NO:1) motif: . . . SGC, SGN, or SAN
NAALADase: 59 AA's downstream from STQK (SEQ ID NO:3) motif: SFG
>dbj|AP000648.2: SFG
Active site III:
PBP: 111 AA's downstream from SGC motif: . . . KTG
NAALADase: 110 AA's downstream from SFG motif: KLG
>dbj|AP000648.2: KLG Active site IV:
PBP:41 AA's downstream from SGC motif: . . . ENKD (SEQ ID NO:2)
NAALADase: 41 AA's downstream from SFG motif: ERGV (SEQ ID NO:4)
>dbj|AP000648.2: ERSI (SEQ ID NO:6)

4) >gb|AC074003.2|AC074003 Homo sapiens chromosome 2 clone RP11.
Active site I:
PBP: 35 AA's downstream from N-terminus: . . . STTK (SEQ ID NO:1)
NAALADase: 38 AA's downstream from N-terminus: STQK (SEQ ID NO:3)
gb|AC074003.2|AC074003: STQ-
Active site II:
PBP: 57 AA's downstream from STTK (SEQ ID NO:1) motif: . . . SGC, SGN, or SAN
NAALADase: 59 AA's downstream from STQK (SEQ ID NO:3) motif: SFG
gb|AC074003.2|AC074003: SFG
Active site III:
PBP: 111 AA's downstream from SGC motif: . . . KTG
NAALADase: 110 AA's downstream from SFG motif: KLG
gb|AC074003.2|AC074003: KLG
Active site IV:
PBP:41 AA's downstream from SGC motif: . . . ENKD (SEQ ID NO:2)
NAALADase: 41 AA's downstream from SFG motif: ERGV (SEQ ID NO:4)
gb|AC074003.2|AC074003 ERGV (SEQ ID NO:4)

5) >emb|AL162372.6|AL162372 Homo sapiens chromosome 13 clone RP.
Active site I:
PBP: 35 AA's downstream from N-terminus: . . . STTK (SEQ ID NO:1)
NAALADase: 38 AA's downstream from N-terminus: STQK (SEQ ID NO:3)
emb|AL162372.6: STQ-
Active site II:
PBP: 57 AA's downstream from STTK (SEQ ID NO:1) motif: . . . SGC, SGN, or SAN
NAALADase: 59 AA's downstream from STQK (SEQ ID NO:3) motif: SFG
emb|AL162372.6: SFG
Active site III:
PBP: 111 AA's downstream from SGC motif: . . . KTG
NAALADase: 110 AA's downstream from SFG motif: KLG
emb|AL162372.6: KLG
Active site IV:
PBP:41 AA's downstream from SGC motif: . . . ENKD (SEQ ID NO:2)
NAALADase: 41 AA's downstream from SFG motif: ERGV (SEQ ID NO:4)
emb|AL162372.6 ERGV (SEQ ID NO:4)

6) gb|AC024234.51AC024234 Homo sapiens chromosome 11 clone RP1.
Active site I:
PBP: 35 AA's downstream from N-terminus: . . . STTK (SEQ ID NO:1)
NAALADase: 38 AA's downstream from N-terminus: STQK (SEQ ID NO:3)

gb|AC024234.5|AC024234: STQ-Active site II:
PBP: 57 AA's downstream from STTK (SEQ ID NO:1) motif: . . . SGC, SGN, or SAN
NAALADase: 59 AA's downstream from STQK (SEQ ID NO:3) motif: SFG
gb|AC024234.51AC024234: SFG
Active site III:
PBP: 111 AA's downstream from SGC motif: . . . KTG
NAALADase: 110 AA's downstream from SFG motif: KLG
gb|AC024234.5|AC024234: KLG
Active site IV:
PBP:41 AA's downstream from SGC motif: . . . ENKD (SEQ ID NO:2)
NAALADase: 41 AA's downstream from SFG motif: ERGV (SEQ ID NO:4)
gb|AC024234.5|AC024234 ERGV (SEQ ID NO:4)
7) dbj|AP002369.1|AP002369 Homo sapiens chromosome 11 clone RP
Active site I:
PBP: 35 AA's downstream from N-terminus: . . . STTK (SEQ ID NO: 1)
NAALADase: 38 AA's downstream from N-terminus: STQK (SEQ ID NO:3)
dbj|AP002369.1: STQ-
Active site II:
PBP: 57 AA's downstream from STTK (SEQ ID NO:1) motif: . . . SGC, SGN, or SAN
NAALADase: 59 AA's downstream from STQK (SEQ ID NO:3) motif: SFG
dbj|AP002369.1: SFG
Active site III:
PBP: 111 AA's downstream from SGC motif: . . . KTG
NAALADase: 110 AA's downstream from SFG motif: KLG
dbj|AP002369.1: KLG
Active site IV:
PBP:41 AA's downstream from SGC motif: . . . ENKD (SEQ ID NO:2)
NAALADase: 41 AA's downstream from SFG motif: ERGV (SEQ ID NO:4)
dbj|AP002369.1 ERGV (SEQ ID NO:4)

The encoded protein of each of those gene sequences expressed in the brain are probable targets for behavioral and cognitive activity by β-lactams and other NAALADase inhibitors. Thus in accordance with one aspect of ths invention there is provided a method for modifying behavior and/or cognition comprising the step of inhibiting the biological activity of the non-NAALADase protein(s) expressed by one or more of the above-identified gene sequences, by administering an effective amount of a β-lactam compound or other compound capable of NAALADase inhibition.

In one embodiment the NAALADase inhibitors effective for use in the various pharmaceutical formulation and method embodiments of this invention, generally speaking, are compounds which exhibit detectable selective affinity for art recognized penicillin-binding proteins, including particularly β-lactam-containing compounds (hereinafter "β-lactam compounds") such as β-lactamase inhibitors, more particularly clavulanic acid and derivatives thereof. Among such NAALADase inhibiting compounds, those preferred for use in accordance with this invention are compounds that also exhibit good blood brain barrier transport properties evidenced by favorable cerebral spinal fluid (CSF)/brain:serum concentration ratios. Further, it will be appreciated that other art-recognized NAALADase inhibitors can be used alone or in combination with penicillin protein-binding compounds for treatment and prevention of behavioral and/or cognitive disorders.

In the embodiments of the invention directed to pharmaceutical formulations for use in inhibition of neurogenic NAALADase to modify behavior and/or improve cognitive function, the β-lactam compounds are typically formulated in unit dosage form optionally in combination with, or as covalent conjugates of, other compounds or molecular entities, respectively, known to enhance drug transport across the blood brain barrier. Such drug formulation/conjugation techniques are described and claimed in the following listed United States Patents, the specifications of which patents are expressly incorporated herein by reference: U.S. Pat. Nos. 5,624,894; 5,672,683; 5,525,727; 5,413,996; 5,296,483; 5,187,158; 5,177,064; 5,082,853; 5,008,257; 4,933,438; 4,900,837; 4,880,921; 4,824,850; 4,771,059; and 4,540,564.

Enhanced concentrations of drug substances, including NAALADase inhibitors in the brain, can also be achieved by co-administration with P-glycoprotein efflux inhibitors such as those described in U.S. Pat. Nos. 5,889,007; 5,874,434; 5,654,304; 5,620,855; 5,643,909; and 5,591,715, the specifications of which patents are expressly incorporated herein by reference. Alternatively, useful β-lactam antibiotic compounds, including penicillins, cephalosporins, penems, 1-oxa-1-dethia cephems, clavams, clavems, azetidinones, carbapenams, carbapenems, and carbacephems, can be administered in combination with clavulanate. Examples of other β-lactamase inhibitors which can be used in combination with clavulanate derivatives useful in accordance with this invention for treatment and/or prevention of cognitive or behavioral disorders are other β-lactam compounds which may or may not exhibit independent antibacterial activity, such as thienamycin and analogs thereof, sulbactam, tazobactam, sultamicillin, and aztreonam and other monolactams.

The patent and non-patent literature is replete with references describing β-lactam antibiotics, their preparation, their characterization, their formulation and their mode of action. β-Lactam antibiotics are known to exhibit their antibiotic activity by interfering with one or more biological pathways involved in bacteria cell wall synthesis; more particularly, they inhibit carboxypeptidase and/or transpeptidase (or protease) activity involved in cross-linking of the peptidoglycan chains used as building blocks for cell wall synthesis. β-Lactam antibiotics are thus believed to act as inhibitors of carboxypeptidases or transpeptidases by their covalent, and by some reports, noncovalent associative bonding, to one or more of a group of such bacterial enzymes generally termed penicillin binding proteins (PBP's). Such enzymes serve to complete bacteria cell wall synthesis by cross linking peptidoglycan chains.

A similar peptidase-substrate interaction/inhibition is now suggested in accordance with this invention as a significant neurochemical pathway involved in brain function pivotal to cognitive performance and behavioral phenotype. Such a neurochemical mechanism is suggested too by the discovery that delivery of effective amounts of the peptide Ala-D-γ-Glu-Lys-D-alanyl-D-alanine directly into the brain produced the same modified behavioral characteristics as that achieved by comparable concentrations of β-lactam compounds in the brain. The peptide appears to serve as a substitute substrate for (and thus serve to inhibit the activity thereof) one or more neurogenic peptidases (e.g., NAALADases) that normally exhibit their activity on peptidic neurotransmitters or neuromodulators, i.e., NAAD, in the ordinary course of certain neurochemical processes that mediate cognitive performance and behavioral phenotype.

Based on animal tests to date it is believed that the general classes of behavioral disorders can be prevented or treated in accordance with this invention by administration of effective amounts of NAALADase inhibitors include aggressive disorder, obsessive-compulsive disorder, anxiety, depression, and attention deficit hyperactivity disease (ADHD). Thus in one embodiment of the invention a NAALADase inhibitor selected from those capable of binding to penicillin-binding protein, e.g., a β-lactam antibiotic or β-lactamase inhibitor, and/or those exhibiting inhibition of selective proteolytic activity on a bacterial protein or peptide substrate comprising the C-terminal amino acid sequence acyl-D-alanyl-D-alanine, or other NAALADase inhibitor, is administered as an anti-aggressive agent to control impulsivity and violence in a patient afflicted with autism, Tourette's Syndrome, mental retardation, psychosis, mania, senile dementia or that in a patient with personality disorder and history of inappropriate aggression. In another embodiment a deaminoglutamate analog or an N-substituted glutamate derivative is administered in an amount effective to control impulsivity and violence in patients effected with such disease states.

Other neurological disease states which can be treated in accordance with the present invention include depression, including major depression (single episode, recurrent, melancholic), atypical, dysthmia, subsyndromal, agitated, retarded, co-morbid with cancer, diabetes, or post-myocardial infarction, involutional, bipolar disorder, psychotic depression, endogenous and reactive, obsessive-compulsive disorder, or bulimia. In addition, NAALADase inhibitors can be used to treat patients suffering from pain (given alone or in combination with morphine, codeine, or dextroproposyphene), obsessive-compulsive personality disorder, post-traumatic stress disorder, hypertension, atherosclerosis, anxiety, anorexia nervosa, panic, social phobia, stuttering, sleep disorders, chronic fatigue, cognition deficit associated with Alzheimer's disease, alcohol abuse, appetite disorders, weight loss, agoraphobia, improving memory, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of other antidepressants, aggressive/intermittent explosive disorder, compulsive gambling, compulsive spending, compulsive sex, psychoactive substance use disorder, sexual disorder, schizophrenia, premature ejaculation, or psychiatric symptoms selected from stress, worry, anger, rejection sensitivity, and lack of mental or physical energy.

Other examples of pathologic, psychologic conditions which may be treated in accordance with this invention include, but are not limited to: Moderate Mental Retardation (318.00), Severe Mental Retardation (318.10), Profound Mental Retardation (318.20), Unspecified Mental Retardation (319.00), Autistic Disorder (299.00), Pervasive Developmental Disorder NOS (299.80), Attention-Deficit Hyperactivity Disorder (314.01), Conduct Disorder, Group Type (312.20), Conduct Disorder, Solitary Aggressive Type (312.00), Conduct Disorder, Undifferentiated Type (312.90), Tourette's Disorder (307.23), Chronic Motor or Vocal Tic Disorder (307.22), Transient Tic Disorder (307.21), Tic Disorder NOS (307.20), Primary Degenerative Dementia of the Alzheimer Type, Senile Onset, Uncomplicated (290.00), Primary Degenerative Dementia of The Alzheimer Type, Senile Onset, with Delirium (290.30), Primary Degenerative Dementia of the Alzheimer Type, Senile Onset, with Delusions (390.20), Primary Degenerative Dementia of the Alzheimer Type, Senile Onset, with Depression (290.21), Primary Degenerative Dementia of the Alzheimer Type, Presenile Onset, Uncomplicated (290.10), Primary Degenerative Dementia of the Alzheimer Type, Presenile Onset, with Delirium (290.1 1), Primary Degenerative Dementia of the Alzheimer Type, Presenile Onset, with Delusions (290.12), Primary Degenerative Dementia of the Alzheimer Type, Presenile Onset, with Depression (290.13), Multi-infarct dementia, Uncomplicated (290.40), Multi-infarct dementia, with Delirium (290.41), Multi-infarct Dementia, with Delusions (290.42), Multi-infarct Dementia, with Depression (290.4 3), Senile Dementia NOS (290.10), Presenile Dementia NOS (290.10), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Hood Disorder (292.84), Phencyclidine (PCP) or Similarly Acting Arylcyclohexylamine Organic Mental Disorder NOS (292.90), Other or unspecified Psychoactive Substance Intoxication (305.90), Other or Unspecified Psychoactive Substance Delirium (292.8 1), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.81), Organic Mood Disorder (293.83), Organic Anxiety Disorder (294.80), Organic Personality Disorder (310.10), Organic Mental Disorder (29.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39).

Additional examples of pathologic psychological conditions which may be treated using protease inhibitors as described in this invention include Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic 295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, unspecified (295.60), Delusional (Paranoid) Disorder (297.10), Brief Reactive Psychosis (298.80), Schizophreniform Disorder (295.40), Schizoaffective Disorder (295.70), induced Psychotic Disorder (297.30), Psychotic Disorder NOS (Atypical Psychosis) (298.90), Bipolar Disorder, Mixed, Severe, without Psychotic Features (296.63), Bipolar Disorder, Manic, Severe, without Psychotic Features (296.43), Bipolar Disorder, Depressed, Severe, without Psychotic Features (296.53), Bipolar Disorder, Mixed, with Psychotic Features (296.64), Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), Major Depression, Recurrent with Psychotic Features (296.34) Personality Disorders, Paranoid (301.00), Personality Disorders, Schizoid (301.20), Personality Disorders, Schizotypal (301.22), Personality Disorders, Antisocial (301.70), Personality Disorders, Borderline (301.83).

Anxiety disorders which may be treated in accordance with this invention include, but are not limited to, Anxiety Disorders (235), Panic Disorder (235), Panic Disorder with Agoraphobia (300.21), Panic Disorder without Agoraphobia (300.01), Agoraphobia without History of Panic Disorders (300.22), Social Phobia (300.23), Simple Phobia (300.29), Organic Anxiety Disorder (294.80), Psychoactive Substance Anxiety Disorder (292.89), Separation Anxiety Disorder (309.21), Avoidant Disorder of Childhood or Adolescence (313.21), and Overanxious Disorder (313.00).

Effective amounts of NAALADase inhibitors can be used for the treatment of the following pathologic psychological conditions: Moderate Mental Retardation; Severe Mental Retardation; Profound Mental Retardation; Autistic Disorder; Attention-Deficit Hyperactivity Disorder; Pervasive Development Disorder NOS; Conduct Disorder, Group Type; Conduct Disorder, Solitary Aggressive Type; Tourette's Disorder; Primary Degenerative Dementia of the Alzheimer Type, Senile Onset, with Delirium; Primary Degenerative Dementia of the Alzheimer Type, Senile Onset, with Delusions; Primary Degenerative Dementia of the Alzheimer Type, Presenile Onset; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, or Recurrent with Psychotic Features; Personality Disorders, Paranoid; Personality Disorders, Schizoid; Personality Disorders, Schizotypal; Personality Disorders, Antisocial; Personality Disorders, Borderline, Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder, Post-Traumatic Stress Disorder, Generalized Anxiety Disorder, Anxiety Disorder NOS, Organic Anxiety Disorder, Psychoactive Substance Anxiety Disorder, Separation Anxiety Disorder, Avoidant Disorder of Childhood or Adolescence, and Overanxious Disorder.

One or more neurogenic NAALADase inhibitors, including particularly neurotropic β-lactam antibiotics or β-lactamase inhibitors can be used alone, in combination or in combination with P-glycoprotein inhibitors to treat the following psychotic conditions: Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Personality Disorders, Paranoid; Personality Disorders, Schizoid; Personality Disorders, Schizotypal; Personality Disorders, Antisocial; Personality Disorders, Borderline.

Examples of psychotic conditions which are most preferredly treated in accordance with the method of this invention include Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchornic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Personality Disorders, Schizoid; and Personality Disorders, Schizotypal.

Examples of anxiety disorders which are treated using the present method and pharmaceutical formulations of this invention, include Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder, Post-Traumatic Stress Disorder, Generalized Anxiety Disorder, Anxiety Disorder NOS, Organic Anxiety Disorder, Psychoactive Substance Anxiety Disorder, Separation Anxiety Disorder, Avoidant Disorder of Childhood or Adolescence, and Overanxious Disorder.

Examples of the anxiety disorders which are most preferredly treated include Panic Disorder; Social Phobia; Simple Phobia; Organic Anxiety Disorder; Obsessive Compulsive Disorder; Post-traumatic Stress Disorder; Generalized Anxiety Disorder; and Anxiety Disorder NOS.

The NAALADase inhibitors used as the neurochemically functional agent in the methods and formulations of the present invention are, in one embodiment of the invention, characterized particularly by their binding to penicillin-binding proteins [as determined using methods described, for example, by B. G. Spratt, Properties of the penicillin-binding proteins of *Escherichia coli* K12, Eur. J. Biochem., 72:341–352(1977) and N. H. Georgopapadakou, S. A. Smith, C. M. Cimarusti, and R. B. Sykes, Binding of monolactams to penicillin-binding proteins of *Escherichia coli* and *Staphylococcus aureus*: Relation to antibacterial activity, Antimocrob. Agents Chemother., 23:98–104(1983)] and, in the case of antibiotics, by their inhibition of selective carboxypeptidase and/or transpeptidase activity on peptide substrates comprising the amino acid sequence Ala-D-γ-Glu-Lys-D-alanyl-D-alanine. Such compounds include particularly, β-lactam compounds. Preferred β-lactam compounds are penicillins, cephalosporins, and monocyclic and bicyclic analogs and/or derivatives thereof. Commercially available β-lactam antibiotics include penams, cephems, 1-oxa-1-dethia cephems, clavams, clavems, azetidinones, carbapenams, carbapenems and carbacephems.

In the preferred embodiments of the present invention the neurologically active peptidase inhibitor is clavulanic acid or pharmaceutically acceptable salts or ester (for example, active ester) forms thereof. Such compounds and numerous structurally related compounds reported to have similar β-lactamase/antibiotic activity are well known in the art. Such derivatives are, for the purposes of this invention, included within the term clavulanate as used in describing this invention. Active esters of clavulanates can be prepared to enhance oral absorption.

Examples of suitable in vivo hydrolysable (active) ester groups include, for example, acyloxyalkyl groups such as acetoxymethyl, pivaloyloxymethyl, β-acetoxyethyl, β-pivaloyloxyethyl, 1-(cyclohexylcarboonyloxy) prop-1-yl, and (1-aminoethyl) carbonyloxymethyl; alkoxycarbonyloxyalkyl groups, such as ethoxycarbonyloxymethyl and alpha-ethoxycarbonyloxyethyl; dialkylaminoalkyl groups, such as ethoxycarbonyloxymethyl and β-ethoxycarbonyloxyethyl; dialkylaminoalkyl especially di-lower alkylamino alkyl groups such as dimethylaminomethyl, dimethylaminoethyl, diethylaminomethyl or diethylaminoethyl-2-(alkoxycarbonyl)-2-alkenyl groups such as 2-(isobutoxycarbonyl) pent-2-enyl and 2-(ethoxycarbonyl)but-2-enyl; lactone groups such as phthalidyl and dimethoxyphthalidyl; and esters linked to a second β-lactam antibiotic or to a β-lactamase inhibitor. One example of such chemical modification of a commercially available parenteral β-lactam antibiotic is the preparation of the bis-indanyl ester of moxalactam.

Suitable pharmaceutically acceptable salts of the clavulanate carboxy group include metal salts, e.g., aluminum, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, -ethylpiperidine, N-benzyl-β-phenethylamine, dehydroabietylamine, N.N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

Those β-lactam compounds detailed for parenteral administration can be modified, as indicated above, as their active ester derivatives to improve oral absorption with the goal of attaining brain levels of the compound sufficient to inhibit neurogenic protease, but not necessarily sufficient to provide clinically effective antibiotic blood levels.

Other related clavulanate compounds capable of neurogenic peptidase inhibition via the mechanism proposed for the activity of β-lactam compounds can be identified using art recognized molecular discovery techniques, for example, that described in U.S. Pat. No. 5,552,543, the specification of which is expressly incorporated by reference. That patent described algorithms for detecting correlation between antibacterial activity and the "lock and key" interactions which take place between penicillin-binding proteins and β-lactam antibiotics. Such molecular modeling techniques can be correlated with other drug modeling techniques (for example that described in published PCT International Application No. WO 99/10522, the text of which is expressly incorporated herein by reference) for identifying compounds with good blood-brain barrier transport efficacies to identify optimally effective compounds for use in accordance with the embodiments of this invention. Thus, for treatments in accordance with this invention targeting neurogenic NAALADase, it is not only important that compounds useful in this invention are active as inhibitors of the targeted neurological protease (NAALADase), but it is also important that such compounds can be delivered with some threshold degree of efficiency through the blood-brain barrier to provide effective protease inhibiting concentration of the drug in the brain. Such blood-brain barrier transport properties can derive inherently from compound structure, or such compounds can be formulated and/or conjugated with other chemical entities effective to enhance blood-brain barrier transport. There has been a significant research and development effort directed to the preparation and formulation of compounds to enhance their blood-brain barrier transport, and such technologies can be applied to enhance brain concentration of the protease inhibitors and adjuvants therefor useful in accordance with this invention.

Animal tests indicate a threshold effective dose of moxalactam (administered parenterally) to be about 50 βg/kg of body weight. Based on animal test data and on the known distribution of parenterally administered moxalactarn between the brain and other body tissues, that the effective minimum neurogenic protease inhibiting concentration of moxalactam in the brain is about 30 nM. Clavulanic acid, a preferred clavulanate for use in this invention, has been shown to be an effective inhibitor of neurogenic NAALADase when administered i.p. at less than 1 microgram per kilogram of body weight. The range of effective dosage levels of the NAALADase inhibitors when used in the treatment of behavioral and/or cognitive disorders in accordance with this invention will depend significantly on patient body weight, the affinity of the inhibitor for the target neurogenic protease, the blood-brain barrier transport characteristics of the active compound, the mode of administration and the optional use of available drug formulations/conjugation technologies available for enhancement of blood-brain barrier transport. For parenterally administered moxalactam the minimum effective dose in hamsters and other test species is about 50 micrograms per kg of body weight, more or less. The use of moxalactam in an oral dosage form, preferably modified or derivatized in the form of an active ester, is estimated to range from about 2.5 to about 50 mg per dose, much less than the dose of moxalactam necessary to provide therapeutically effective antibiotic concentration. The effective oral dose of clavulanate is expected to be about 0.1 to about 10 mgs per dose. Clavulanic acid is orally absorbed and it exhibits good blood brain barrier transport.

The effective doses of other related β-lactam compounds will vary, again depending on their inherent affinity for the target protease, the selected route of administration, patient weight, and blood-brain barrier transport efficiency. The effective dosages of NAALADase inhibitors used in accordance with the present invention can be readily determined empirically using animal models coupled with use of art recognized analytical techniques. Typically, the dosage levels for β-lactam antibiotic compounds is less than that necessary to achieve clinically effective antibacterial levels. Parenteral dosages of β-lactam antibiotic compounds can range from about 1 to about 80 mg per dose. Oral dosages can range from about 2.5 to about 250 mg per dose. Higher or lower dosage amounts may be appropriate and used in accordance with this invention when patient circumstances dictate such in the judgement of the attending physician. Thus, for example, where patient/clinical conditions are such that the inherent antibiotic activity of the β-lactam compounds are not considered to be a complicating contraindication, higher doses of the antibiotic up to or exceeding the dosage levels capable of providing threshold clinically effective antibiotic blood levels can be used to treat patients in need of therapy effected by NAALADase inhibition in accordance with this invention.

Other art-recognized NAALADase inhibitors capable of crossing the blood brain barrier in effective amounts can be used for treatment of behavioral and cognitive disorders. For example, they can be used to improve cognitive performance in patients afflicted with dementia or to reduce aggession. Examples of known NAALADase inhibitors include general metallopeptidase inhibitors such as O-phenanthroline, metal chelators such as ethylenediaminetetracetic acid (EDTA) and ethyleneglycol-bis (betaminoethylether)-N,N-tetracetic acid (EGTA) and peptide analogs such as quesqualic acid, aspartate glutamate (Asp-Glu), Glu-Glu, Gly-Glu, γ-Glu-Glu and beta-N-acetyl-L-aspartate-L-glutamate. Other NAALADase inhibitors are the more recently described compounds of the formula

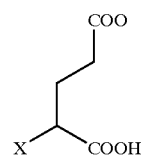

wherein X is RP(O)(OH)CH$_2$— [See U.S. Pat. No. 5,968,915 incorporated herein by reference]; RP(O)(OH)NH— [See U.S. Pat. No. 5,863,536 incorporated herein by reference]; RP(O)(OH)O— [See U.S. Pat. No. 5,795,877 incorporated herein by reference]; RN(OH)C(O)Y— or RC(O)NH(OH)Y wherein Y is $CR_1R_2$, $NR_3$ or O [See U.S. Pat. No. 5,962,521 incorporated herein by reference]; or X is RS(O)Y, $RSO_2Y$, or RS(O)(NH)Y wherein Y is $CR_1R_2$, $NR_3$ or O [See U.S. Pat. No. 5,902,817 incorporated herein by reference].

Each of the above-mentioned U.S. patents suggest uses of the described NAALADase inhibitors in treatment of disease states associated with glutamate abnormality including epilepsy, stroke, Alzheimer's disease, Parkinson's disease, Amyotrophic Lateral Sclerosis (ALS), Huntington's disease, schizophrenia, chronic pain, ischemia and neuronal insult. The discovery underlying the present invention enables use of inhibitors of penicillin binding protein (bacterial carboxypeptidase or transpeptidase) particularly β-lactam antibiotics and β-lactamase inhibitors for developing therapeutic protocols for such disease states based on the previously unappreciated activity of such compounds as NAALADase inhibitors. More recently high concentrations of glutamate in nervous tissues have been associated with multiple sclerosis, and it is contemplated that inhibition of NAALADase in such tissues and consequently inhibition of its production of glutamate can provide therapeutic benefit to patients afflicted with the disease by either reducing the severity of the symptoms or by reducing the occurrence of their onset.

The present invention further provides certain pharmaceutical formulations for treatment of behavioral or cognitive disorders and other disease states associated with production of abnormal glutamate concentrations in nervous tissues and other tissues harboring NAALADase activity. Generally the formulation comprises a neurologically active clavulanate capable of inhibiting a bacterial enzyme and capable of inhibiting a neurogenic peptidase (NAALADase) that is known, by empirical evidence, to selectively act on a peptide comprising the amino acid sequence Ala-D-γ-Glu-Lys-D-alanyl-D-alanine, and a pharmaceutically acceptable carrier therefor. In one embodiment the pharmaceutical formulation in a unit dosage form comprises an amount of a clavulanate compound capable of inhibiting NAALADase activity in a patient experiencing or disposed to develop a medical condition that could be prevented or treated to reduce its symptoms by NAALADase inhibition. The amount of the peptidase (NAALADase) inhibitor and the nature of the carrier is dependent, of course, on the intended route of administration. The amount of inhibitor is that amount effective to provide upon delivery by the predetermined route of administration, a concentration of the inhibitor in the tissue where NAALADase inhibition is desired, e.g., in the brain effective to treat and reduce symptoms of the targeted behavioral or cognitive disorders or other disorders than can be treated by inhibition of NAALADase activity. In embodiments utilizing β-lactam antibiotic compounds the amount of the peptidase inhibitor in the present formulations is typically less than that capable of providing clinically effective bacterial protease inhibition, i.e., less than that capable of providing antibiotically effective levels when administered to a patient in the dosage form provided. The clavulanate compounds for use in accordance with this invention can be combined with one or more pharmaceutically acceptable carriers, and may be administered, for example, orally in such forms as tablets, capsules, caplets, dispersible powders, granules, lozenges, mucosal patches, sachets, and the like. The NAALADase inhibitor can be combined with a pharmaceutically acceptable carrier, for example starch, lactose or trehalose, alone or in combination with one or more tableting excipients and pressed into tablets or lozenges. Optionally, such tablets, caplets or capsules can be enterically coated to minimize hydrolysis/degradation in the stomach. Oral dosage formulations contain about 1 to about 99% by weight active ingredient and about 1 to about 99% of a pharmaceutically acceptable carrier and/or formulating excipients. Optionally, when β-lactam antibiotics are used as the NAALADase inhibitors the dosage forms can be formulated by combining it with a P-glycoprotein inhibitor or a β-lactamase inhibitor, or both, to provide enhanced drug half-life and brain concentrations of the active ingredient. Alternatively, the protease inhibitor can simply be co-administered with a P-glycoprotein or β-lactamase inhibitor; or the dosage form can comprise a β-lactamase inhibitor (itself also a NAALADase inhibitor) alone or in combination with a P-glycoprotein and a carrier.

In another embodiment of the invention pharmaceutical preparations may contain, for example, from about 2.5% to about 90% of the active ingredient in combination with the carrier, more usually between about 5% and about 60% by weight active ingredient. The pharmaceutical formulations in accordance with one embodiment of this invention are formulated for per os administration, i.e., oral ingestion administration or buccal or sublingual administration (in the form of sachets, lozenges, and/or oral mucosal patches). In another embodiment the dosage form is formulated for per os administration is in a prolonged release dosage form formulated to release the active ingredient over a predetermined period of time.

Topical, dosage forms, including transdermal patches, intranasal, and suppository dosage unit formulations containing the active protease inhibitor and conventional nontoxic pharmaceutically acceptable carriers, adjuvants and vehicles adapted for such routes of administration are also within the scope of this invention.

The pharmaceutical formulations in accordance with this invention alternatively can be delivered via parenteral routes of administration, including subcutaneous administration, intraperitoneal administration, intramuscular administration and intravenous administration. Such parenteral dosage forms are typically in the form of aqueous solutions or dispersions utilizing a pharmaceutically acceptable carrier such as isotonic saline, 5% glucose, or other well known pharmaceutically acceptable liquid carrier composition.

The pharmaceutical forms suitable for injectable use include sterile aqueous solutions or dispersions and sterile powders or lyophilizates for the extemporaneous preparation of sterile injectable solutions or dispersions. In all cases, the dosage form must be sterile and it must be stable under the conditions of manufacture and storage, and must be preserved against the contaminating action of microorganisms. The carrier for injectable formulations can be a solvent or dispersion medium containing, for example, water, ethanol, or a polyol (or example glycerol, propylene glycol and liquid polyethyleneglycol), mixtures thereof, and vegetable oil.

Parenteral dosage forms of the clavulanate compounds useful for treatment of behavioral and cognitive disorders and other disease states responsive to NAALADase inhibition can also be formulated as injectable prolonged release formulations in which the protease inhibitor is combined with one or more natural or synthetic biodegradable or biodespersible polymers such as carbohydrates, including starches, gums and etherified or esterified cellulosic derivatives, polyethers, polyesters (particularly polylactide, polyglycolide or poly-lactide-glycolides), polyvinyl alcohols, gelatins, or alginates. Such dosage formulations can be prepared, for example, in the form of microsphere suspensions, gels (of hydrophilic or hydrophobic constitution), or shaped-polymer matrix implants that are well-known in the art for their function as "depot-type" drug delivery systems that provide prolonged release of the biologically active components. Such compositions can be prepared using art-recognized formulation techniques and designed for any of a wide variety of drug release profiles.

The administration of pharmaceutical compositions for use in the present invention can be intermittent or at a gradual, or continuous, constant or controlled rate to a patient in need of treatment. In addition, the time of day and the number of times of day that the pharmaceutical formulation is administered can vary depending on the patient condition and environment. The level of efficacy and optimal dosage and dosage form for any given protease inhibitor for use within the scope of this invention is patient-dependent and adjustable within reasonable ranges in the judgment of the attending physician. The formulation is typically administered over a period of time sufficient to treat or prevent the patient disease state, e.g., to modify the behavioral or cognitive performance of the patient undergoing treatment. The protease inhibitor formulations may be continued to be administered using the same or attenuated dosage protocol for prophylaxis of the targeted disease state.

EXPERIMENTAL EXAMPLES

While clavulanic acid contains a beta-lactam ring and is structurally similar to penicillins and cephalosporins, it has weak antibacterial activity with no therapeutic value as an antibiotic. However, when given in combination with some beta-lactam antibiotics like ticarcillin (Timentin®) clavulanic acid can extend the spectrum and enhance the activity of the antibiotic (AHFS, 1991). This synergistic activity is possible because clavulanic acid acts as an irreversible competitive inhibitor of bacterial beta-lactamases that naturally degrade and inactive beta-lactam antibiotics (Brown et al., 1976; Reading and Cole 1977).

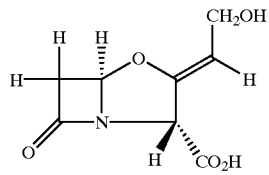

Clavulanic acid is commercially available in the United States but only in fixed combination with other drugs. Commonly prescribed Timentin® is normally given intravenously in doses ranging from 200–300 mg/kg/day (based on ticarcillin content) which corresponds to a dose of clavulanic acid of approximately 7–10 mg/kg/day (AHFS, 1991). There are no reported adverse reactions or contraindications for clavulanic acid given in this dose range (Koyu et al., 1986; Yamabe et al., 1987). The data presented below report clavulanic acid can alter CNS activity and behavior at doses ranging from 10 ng to 10 $\mu$g/kg, or 1000 to 1,00,000 times less than used in antibacterial indications.

Clavulanic acid by itself is orally active and stable. The bioavailability is approximately 64 to 75% (Davies et al., 1985; Bolton et al., 1986) with an elimination half-life of just under two hours. Peak plasma concentrations occur between 45 min to three hours after ingestion (Bolton et al., 1986) with a plasma half-life of over 2 hrs (Nakagawa et al., 1994). The volume of distribution is around 15 liters suggesting clavulanic acid is primarily confined to extracellular fluid (Davies et al., 1985). The CSF/plasma ratio is around 0.25, evidence that clavulanic acid readily passes the blood-brain barrier (Nakagawa et al., 1994).

BEHAVIORAL STUDIES WITH CLAVULANIC ACID

I. Clavulanic Acid Dose-Response in the Seed Finding Model of Anxiety

Rationale

Figure 13:
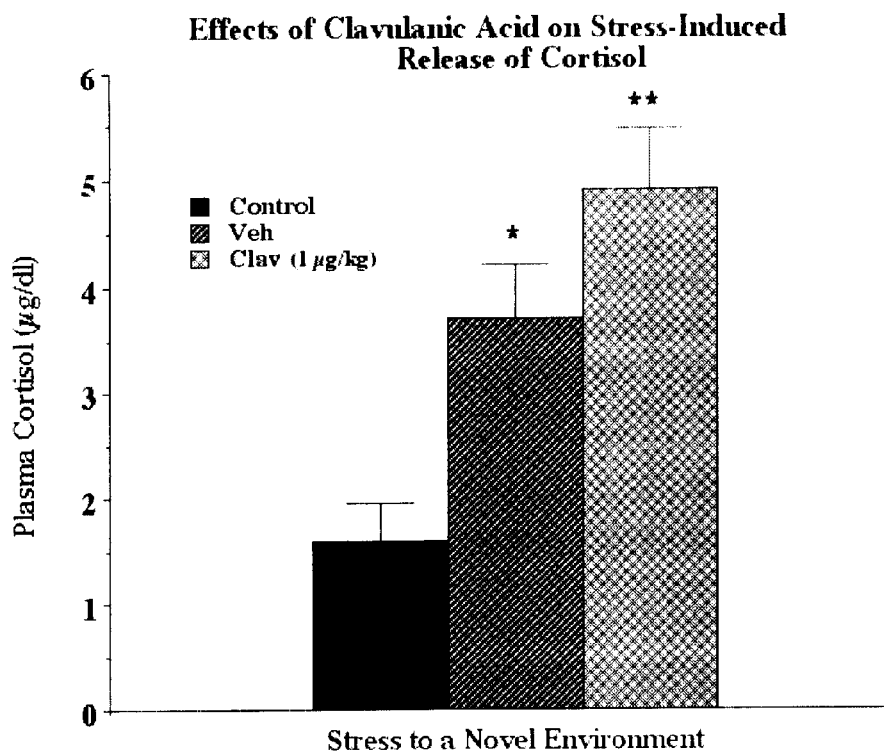

Clavulanic acid (CLAV) is structurally similar to the beta-lactam antibiotics. A most robust and simple bioassay for screening beta-lactams for CNS activity is the golden hamster seed finding model of anxiety. Briefly, hamsters are deprived of food overnight. The following day they are exposed to the additional stress of being taken from their home cage and placed in a novel environment for a few minutes. This manipulation stimulates the release of the stress hormone cortisol (FIG. 13). During their absence from the home cage, sunflower seeds are hidden under the bedding in one of the corners. When returned to the home cage, hamsters routinely scramble along the walls for 1–2 min before settling down, locating and eating the seeds. However, animals treated with the benzodiazepine anxiolytic chlordiazepoxide find seeds in less than 10 sec. This reduction in seed finding time from minutes to seconds also occurs following treatment with moxalactam and other beta-lactam antibiotics.

Experimental Protocol

Male, Syrian golden hamsters (*Mesocricetus auratus*) (120–130 g) obtained from Harlan Sprague-Dawley Laboratories (Indianapolis, Ind.) were housed individually in Plexiglas cages (24 cm×24 cm×20 cm), maintained on a reverse light:dark cycle (14L: 10D; lights on at 19:00 hr) and provided food and water ad libitum. A range of concentrations of CLAV (saline vehicle, 0.1, 1.0, 10, 100 1,000 ng/kg) were tested in six groups of hamsters (4–8/group)(FIG. 1). All tests were conducted during the dark phase of the circadian cycle under dim red illumination. Prior to testing all animals were fasted for 20–24 hrs. Ninety min after intraperitoneal (IP) injection of drug, animals were taken from their home cage and placed into a holding cage for 2 min. During their absence, six sunflower seeds were buried under the bedding in one corner of their home cage. Animals were placed back into their home cage randomly facing any one of the empty corners and timed for their latency to find the seeds in a five min observation period. Latency times were analyzed with a one-way ANOVA followed by Scheffe's post hoc tests. Assumption of equal variances was tested (Hartley's F-max=2.1 p>0.05)

Results

The latency to find the sunflower seeds was significantly different between doses ($F_{(5, 30)}$=10.0; p<0.0001). CLAV in doses of 10 ng and above significantly (p<0.01) reduced latency times to less than 8.0 sec as compared to saline vehicle with a mean latency of 104 sec. The dose of 1 ng/kg was not significantly different from vehicle control.

Summary

The data show CLAV given in a dose of 10 ng/kg body weight has maximal efficacy the seed finding test. The adult male hamsters used in these studies weighed around 125 g. Hence, these animals were given about 1.25 ng of CLAV. CLAV has a volume of distribution approximating the extracellular fluid volume. The extracellular water content of lean body mass is approximately 22%. The concentration of 1.25 ng of CLAV in 27.5 ml of water is 0.045 ng/ml or about 200 pM (formula weight of the potassium salt of CLAV is ca. 240). Since the CSF/plasma ratio is 0.25 the estimated concentration in the brain would be around 50 pM.

The seed finding model of anxiety appears to have empirical validity (McKinney 1989) i.e., drugs like benzodiazepines that are used to treat clinical anxiety are effective in the animal model. However, a wider spectrum of anxiolytics and non-effective drugs must be screened to assess the incidence of false negatives and false positive before adopting seed finding as a model of anxiety. Hence, it was necessary to validate the potential anxiolytic activity of CLAV in the traditional elevated plus-maze.

II. Testing Clavulanic Acid in the Elevated Plus-maze

The elevated plus-maze was developed for screening anxiolytic and anxiogenic drug effects in the rat (Pellow et al., 1985). The method has been validated behaviorally, physiologically, and pharmacologically. The plus-maze consists of two open arms and two enclosed arms. Rats will naturally make fewer entries into the open arms than into the closed arms and will spend significantly less time in open arms. Confinement to the open arms is associated with significantly more anxiety-related behavior and higher stress hormone levels than confinement to the closed arms. Clinically effective anxiolytics, e.g., chlordiazepoxide or diazepam, significantly increase the percentage of time spent in the open arms and the number of entries into the open arms. Conversely, anxiogenic compounds like yohimbin or amphetamines reduce open arm entries and time spent in the open arms.

Experimental Protocol

Male Wistar rats weighing 250–300 g were group housed in a normal 12:12 light-dark cycle with light on at 0800 hr and provided food and water ad libitum. The plus-maze consisted of two open arms, 50 cm long, 10 cm wide, with walls 40 cm high made of clear Plexiglas. The two closed arms had the same dimensions but included a roof. The Plexiglas for the closed arms was painted black. Each pair of arms was arranged opposite to each other to form the plus-maze. The maze was elevated to a height of 50 cm. Eighteen animals were tested in the plus-maze 90 min following the IP injection of 1.0 $\mu$g/kg CLAV, 50 or vehicle control in a volume of ca. 0.3 ml. The order of treatments was counter balanced with at least 48 hrs between injections. At the start of the experiment, the animal was placed at the end of one of the open arms. Over a five min observation period, animals were scored for the latency to enter the closed arm, time spent in the closed arm and the number of open arm entries following the first occupation of the closed arm. The study produced tables of repeated measures. The data between treatments were compared with a two-way, repeated measures ANOVA followed by Bonferroni post hoc tests.

Results

Figure 2A:
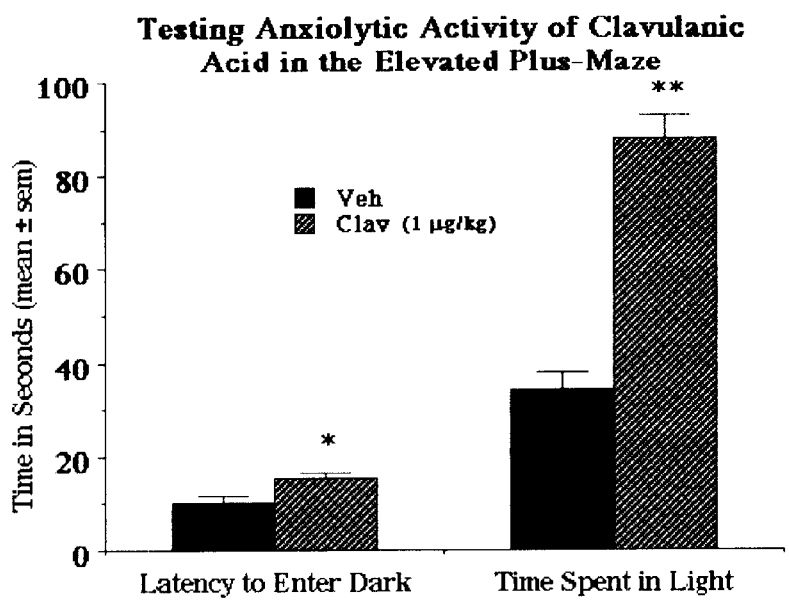
Figure 2B:
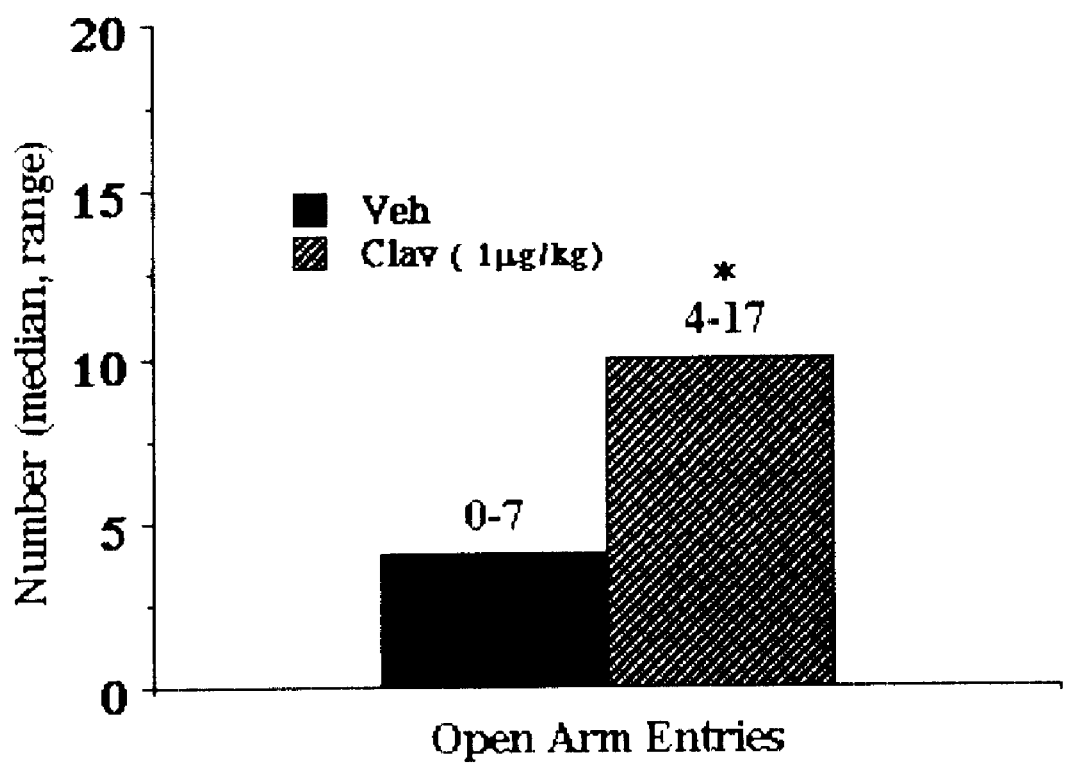

There was a significant difference between treatments for latency to enter the dark ($F_{(1, 18)}=8.53$; $p<0.01$). When treated with CLAV ($p<0.05$) animals stayed in the starting open light position longer than when treated with vehicle (FIG. 26). The time spent in the open arm was highly significant between treatments ($F_{(1, 18)}=144$; $p<0.0001$) (FIG. 2). The time spent in the open arm was significantly increased for CLAV ($p<0.01$) as compared to vehicle. Finally, the open arm entries were significantly different between treatments ($F_{(1, 18)}=44.0$ $p<0.0001$) with CLAV ($p<0.01$) treatment showing increased movement into the lighted open arms as compared to vehicle (FIG. 26).

Summary

These data show CLAV given at a dose of 1 $\mu$g/kg has anxiolytic activity in the plus-maze. These data are encouraging; however, many anxiolytics such as the benzodiazepines depress motor activity. Since animals treated with CLAV took a longer time to move from the lighted open arm to the dark, protected, closed arm it could be argued that this beta-lactam did not reduce anxiety, instead it sedated the animal and retarded movement. To control for this possibility it was necessary to screen CLAV for general motor activity in an open field paradigm.

III. Motor Activity in an Open Field

Experimental Protocol

Figure 3:
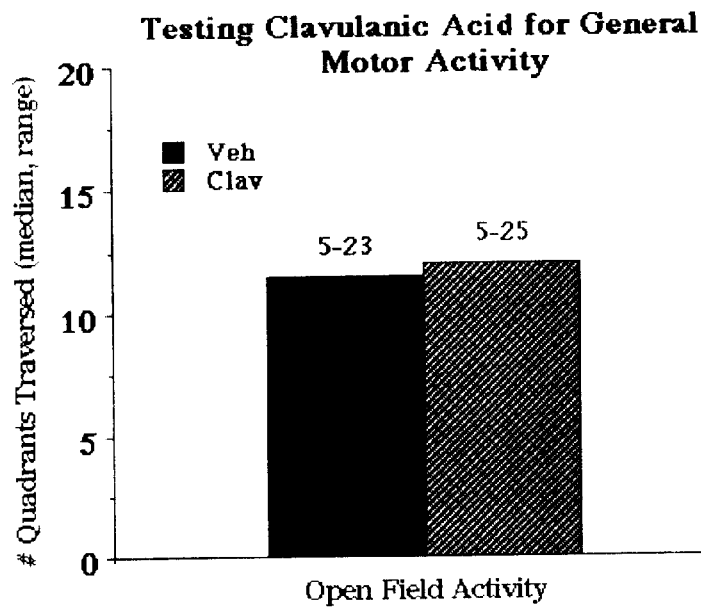

Immediately after each of the plus-maze tests reported above in Section II, animals were tested for general motor activity in an "open field." Animals were placed into a large clean Plexiglas cage (48×32×40 cm) devoid of bedding. This open field was delineated into equal quadrants by tape on the underside of the cage. Animals were scored for motor activity by counting the number of quadrants traversed in 1 min. There were no significant differences between CLAV and vehicle treatment on open field activity (FIG. 3).

Summary

Figure 15:
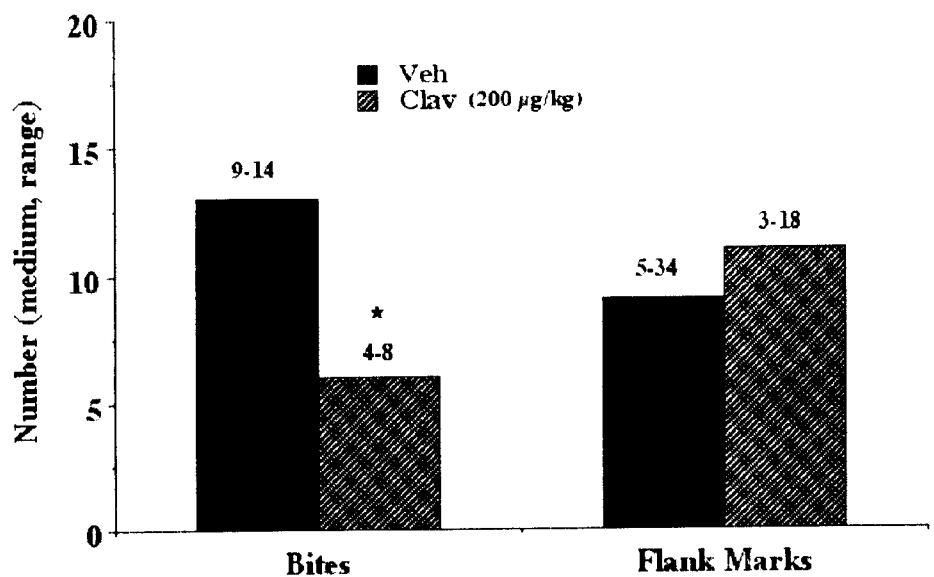

There is no evidence in the open field test that CLAV depress motor activity. This finding is corroborated in another behavioral study, flank marking reported in Section VII. Flank marking is a complex stereotyped motor behavior used by hamsters to disseminate pheromones for olfactory communication (FIG. 15). Flank marking is unaffected by treatments with CLAV. It would appear that this beta-lactam has an advantage over the more conventional benzodiazepine anxiolytics since it does not depress motor activity. However, is the anxiolytic activity of CLAV comparable to the clinically prescribed benzodiazepines?

IV. Clavulanic Acid vs Chlordiazepoxide in the Plus-maze

Experimental Protocol

Chlordiazepoxide (Librium®) is a commonly prescribed anxiolytic that has been thoroughly characterized in preclinical studies. The effective anxiolytic dose in the plus-maze is 10–25 mg/kg (Lister 1987; File and Aranko 1988; Shumsky and Lucki 1994). In this range of doses, chlordiazepoxide (CDP) is a sedative and depresses motor activity complicating the interpretation of any behavioral assay that requires locomotion (McElroy et al., 1985). However, it was discovered animals develop a tolerance to the motor depression with repeated daily administration of CDP for several days (Shumsky and Lucki 1994). Hence in these studies, rats (n=6) were given a single IP injection of CDP (10 mg/kg) each day for seven days prior to the start of the experiment. While CLAV has no effect on motor activity it was necessary to treat an equal number of rats with daily injections of CLAV (100 ng/kg) to insure a balanced experimental design. In addition there was a third group of rats (n=6) receiving daily injections of saline vehicle. The study reported in Section II tested CLAV at 1 $\mu$g/kg in the plus-maze. The data from the seed finding assay of anxiety shown in Section I suggests CLAV should be effective between doses of 10 ng to 1 $\mu$g/kg. For this reason CLAV was tested at 100 ng/kg in these studies.

Results

Figure 4A:
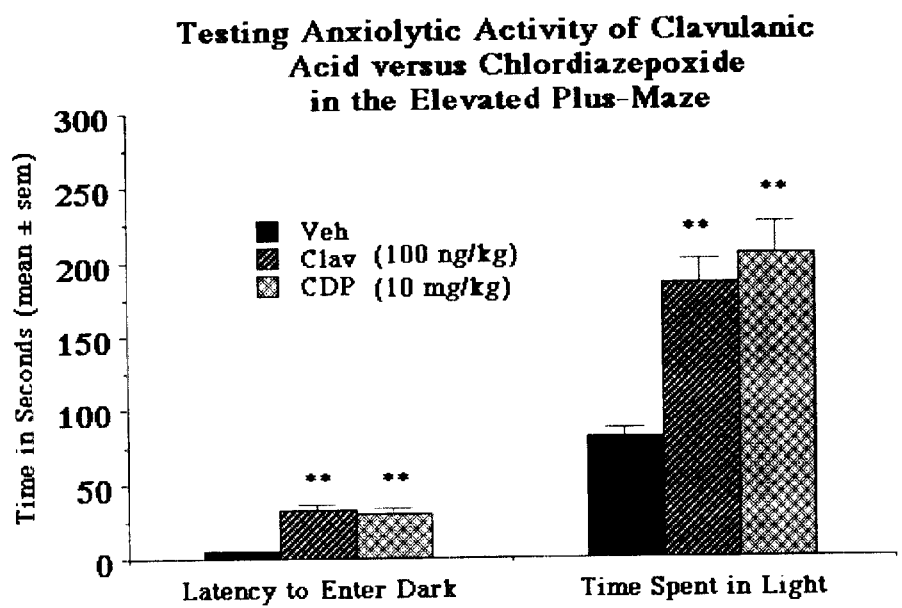
Figure 4B:
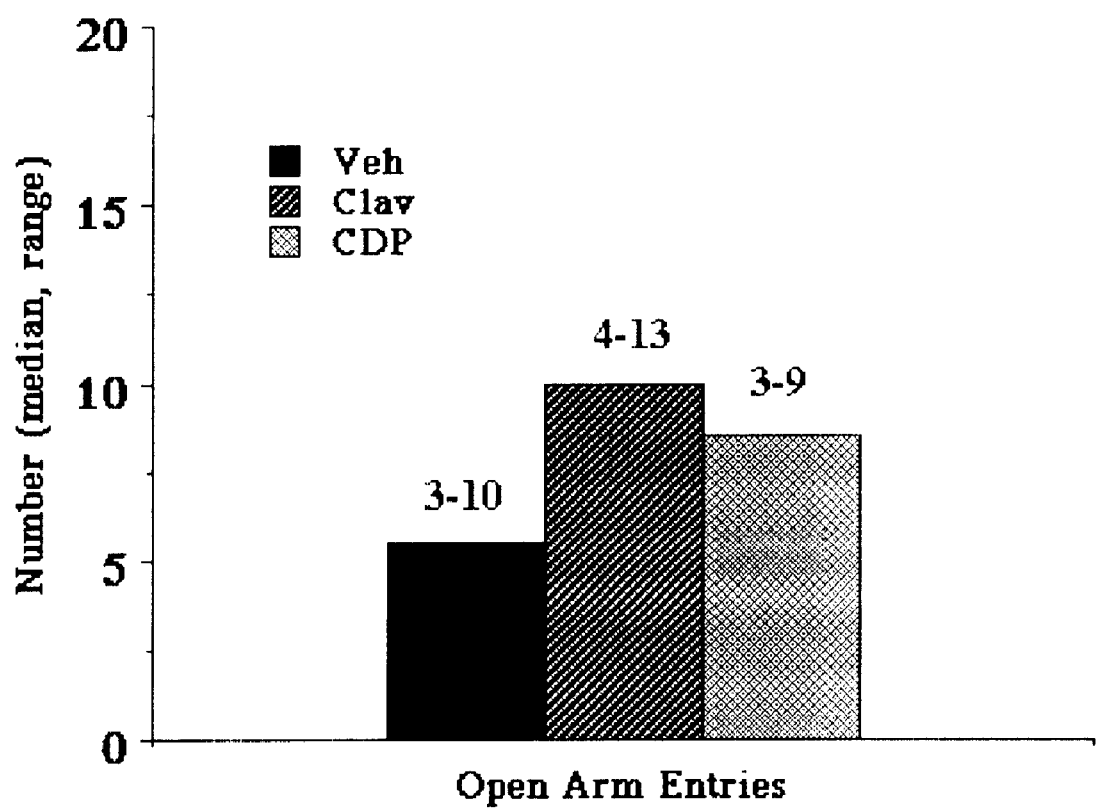

There was a significant difference between treatments ($F_{(2, 15)}=21.45$, $p<0.001$) for the latency to enter the dark. The latency to enter the dark closed arms was significantly greater for animals treated with CLAV and CDP ($p<0.01$) as compared to vehicle control (FIG. 4A). There was also a significant difference between treatments ($F_{(2, 15)}=17.14$, $p<0.001$) for the time spent in the light. The time spent exposed to light in the open arms was also significantly greater for the CLAV and CDP ($p<0.01$) treated animals as compared to vehicle (FIG. 4A). There was no significant difference between treatments for open arm entries (FIG. 4B).

Summary

These data show that CLAV and CDP have similar anxiolytic activity in the elevated plus-maze. Yet, CLAV has greater potency being effective at a dose 100,000 times less than CDP. Furthermore, CLAV does not have the sedative, motor depressant activity of the conventional benzodiazepine anxiolytics. The anxiolytic effects of CLAV are immediate and do not require the development of tolerance to realize behavioral efficacy. However, a point of caution, benzodiazepines have another undesirable side effect for which there is no development of tolerance—amnesia (Shumsky and Lucki 1994). For example, diazepam (Valium®) selectively impairs short-term memory and attention while sparing long-term memory (Liebowitz et al., 1987; Kumar et al., 1987). Hence, it was necessary to test CLAV for any untoward effects on learning and memory.

V. Clavulanic Acid and Spatial Memory in the Water Maze

The Morris water maze was developed to test spatial memory (Morris, 1984). The pool is divided into quadrants usually designated North, South, East and West. The water in the pool is made opaque with milk powder. Hidden just beneath the surface in one of the quadrants is a platform that serves as a escape route for rodents placed into the pool. An animal is placed some where in the pool from a variety of different start points and is timed for latency to find the platform, percent time spent in each quadrant, distance traveled and swimming speed. The animals have no visual or spatial cues in the pool and must rely on extra-maze cues, i.e., objects set up outside the pool that can be seen by the swimming animal. Through a series of trials a rat develops "place learning" or knowledge about the position of the platform based upon the extra-maze cues. The platform can be moved to a different quadrant each day combining spatial memory with working memory. This paradigm involves extinction of the prior memory and resolution of a new spatial problem.

1. Spatial Navigation

Methods

The water maze consisted of a black plastic circular pool ca. 150 cm in diameter and 54 cm in height filled to a level of 35 cm with water made opaque with powdered milk. The pool was divided into four quadrants with a platform 10 cm in diameter submerged 2 cm below the surface in the northwest quadrant. The water was maintained at a temperature of 25° C. Around the pool were several visual cues. Above the pool was a video camera for tracking the movement of the experimental animal. The data collection was completely automated using the software developed by HVS Image (Hampton, UK). Before testing, rats were familiarized with the pool and platform placed in the northwest quadrant. Each day for 4 consecutive days, animals were placed into pool at random sites and given two min to find the platform. Animals were treated one hr before testing with 1.0 µg/kg CLAV (n=9) or vehicle (n=9). Following these familiarization trials, animals were tested for spatial navigation. The first day of testing began with the platform in the expected northwest quadrant. All behavior was videotaped for a two min observation period. After testing the animal were dried off and placed back into their home cage. On each subsequent day the platform was moved to a new quadrant and the rat started at different positions. The rat was always placed into the pool facing the sidewall. The start positions relative to the platform were different for each of the four trials; however, the platform was always in the same relative position in each quadrant. It was positioned 20 cm in from the side of the pool and in the left corner from the center facing out. The latency to find the hidden platform, path length, swim rate, and quadrant times between CLAV and vehicle treated animals were compared with a two-way, repeated measures ANOVA followed by Bonferroni post hoc tests.

Results

Figure 5:
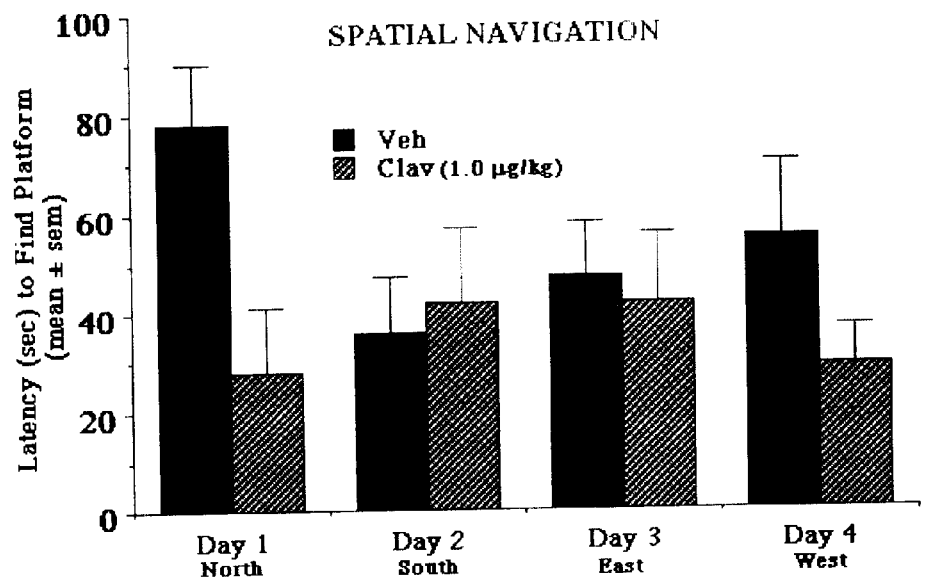

There was no main effect for drug treatment ($F_{(1, 16)}=4.17$, $p<0.057$), days of testing ($F_{(3, 48)}=0.51$, $p>0.5$) or interaction between factors ($F_{(3, 48)}=1.92$ $p>0.1$) (FIG. 5) for latency to find the platform. However, animals treated with CLAV showed shorter latencies to find the platform on Days 1 and 4 with a trend towards significance.

Figure 6A:
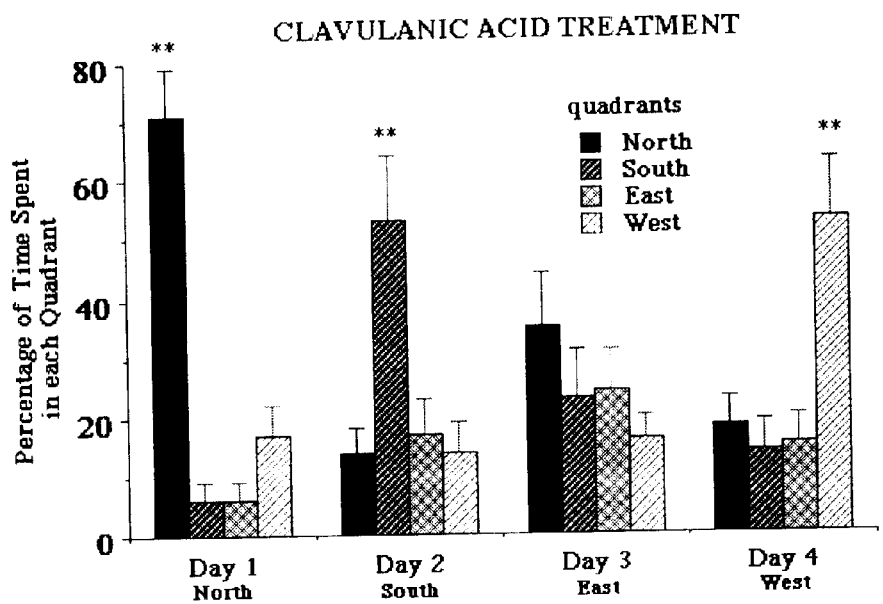
Figure 6B:
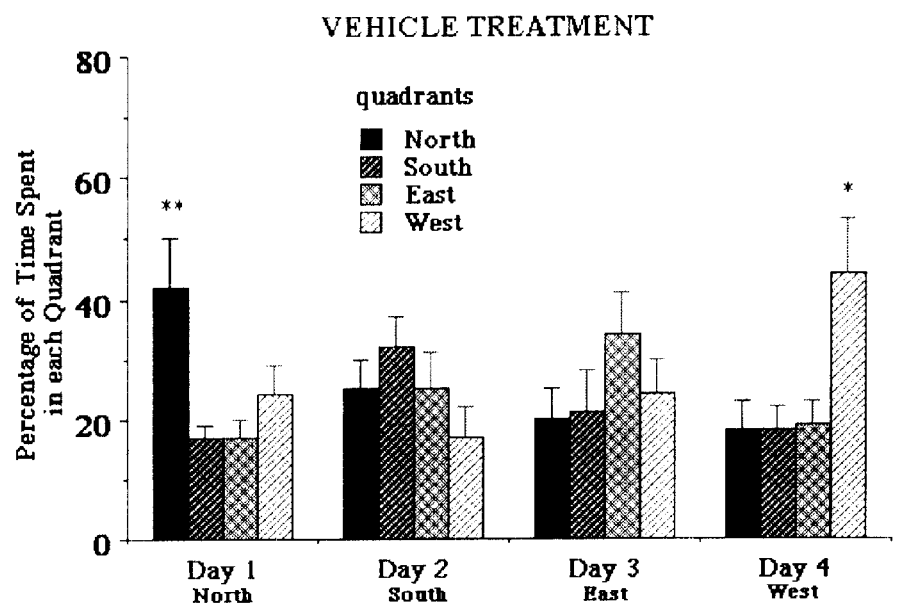

The strategy for finding the platform was similar for both treatments (FIG. 6A & B) as judged by the percentage of time the animals spent in each quadrant. For any quadrant on any day there was no significant difference between treatments. There was a significant difference between days for percentage of time spent in any particular quadrant (e.g., CLAV, North Quadrant, $F_{(3, 32)}=38.81$, $p<0.0001$). Animals spent a significant portion of their time in certain quadrants on certain days. For example, on Day 1 both CLAV and vehicle animals spent most of their time in the North quadrant as compared to the other quadrants ($p<0.01$). This was to be expected since they had knowledge of the location of the platform in this quadrant from the familiarization procedure.

While the strategy for finding the platform as measured by percentage of time spent in each quadrant was similar between CLAV and vehicle there was a small but obvious difference. Animals treated with CLAV spent more time in the correct quadrant than animals treated with vehicle. This difference is particularly true on Day 2 when the CLAV animals spent over 50% ($p<0.01$) of their time in the correct (South) quadrant. The vehicle animals spent less than 40% of their time in the correct quadrant, a time not significantly different from the other quadrants. By Day 4 both CLAV and vehicle spent most of their time in the correct quadrant (West). This strategy on Day 4 shows good spatial, working and procedural memory for both treatments.

Figure 7:
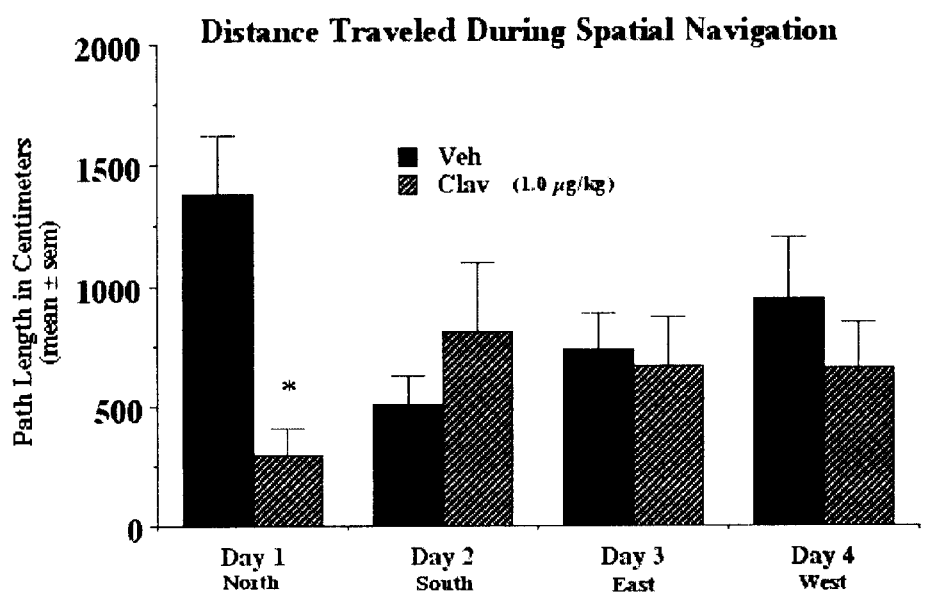
Figure 8:
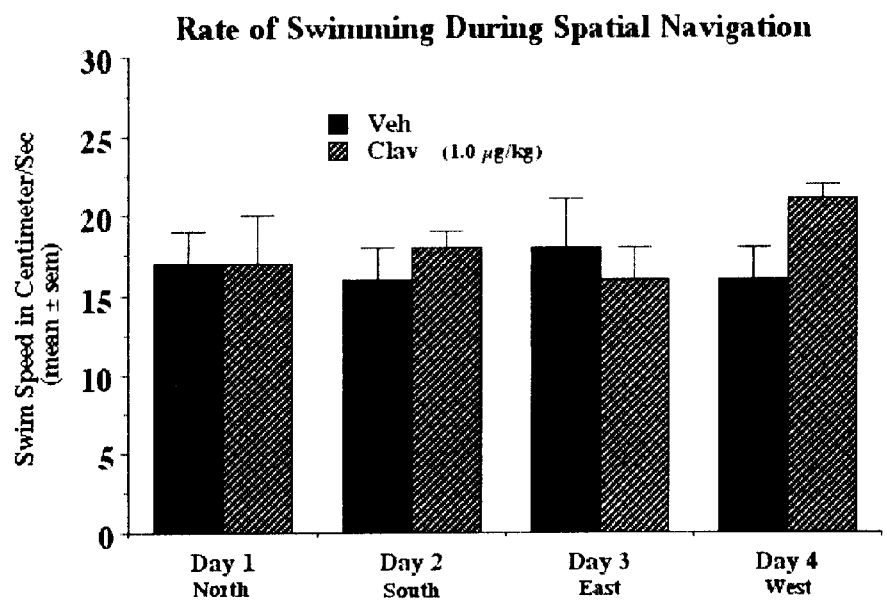

There was a significant main effect for treatment ($F_{(1, 16)}=8.40$, $p>0.01$) on the path length to find the platform. On Day 1 CLAV treated animals ($p<0.05$) traveled a much shorter distance during the search for the platform than vehicle animals (FIG. 7). There was no significant difference between CLAV and vehicle on swim rate (FIG. 8).

2. Cue Navigation

Method

On the day following the last day (Day 4) of spatial navigation, animals were tested for cue navigation. In these tests, the platform was raised above water level. One hr before testing animals were treated with CLAV or saline vehicle. The same animals treated with CLAV during spatial navigation were treated with CLAV for cue navigation. Animals were run through a series of two min trials with 45 min between trials. At each trial, the platform was moved to a different quadrant. The cue navigation study was identical to the spatial navigation except the platform was visible and the testing was done over five consecutive trials done on a single day. Animals were scored for latency to find the platform, percent time spent in each quadrant, path distance and swim speed for all testing periods.

Results

Figure 9:
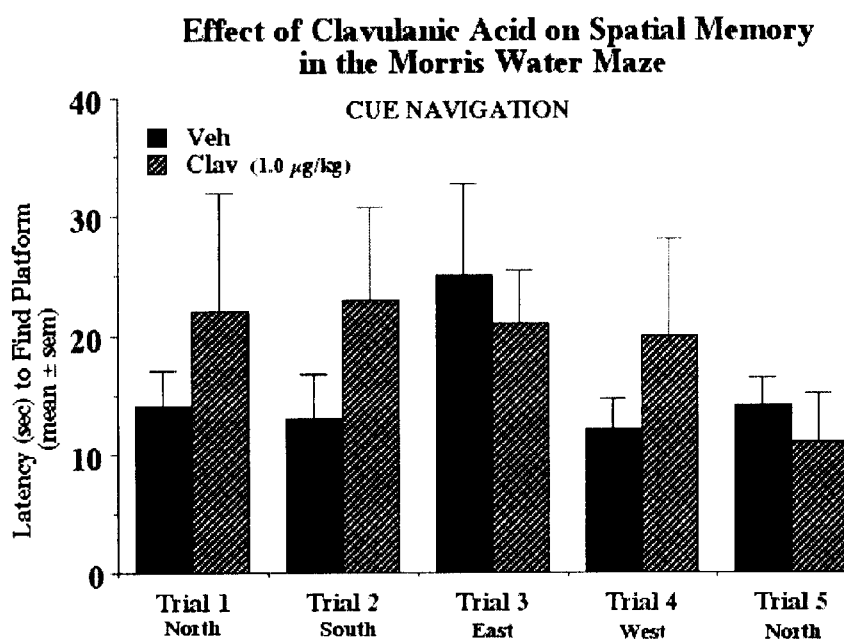

There was no main effect for treatments ($F_{(1, 16)}=0.553$ $p>0.1$), trials ($F_{(4, 64)}=0.9745$, $p>0.1$) or interaction between factors ($F_{(4, 64)}=0.7433$, $p>0.5$) for latency to find the platform during cue navigation (FIG. 9).

As in spatial navigation, the strategy for finding the platform was very similar for both treatments (FIGS. 10 A & B) as judged by the percentage of time the animals spent in each quadrant. For any quadrant on any trial there was no significant difference between treatments (e.g., Trial 1, North, $F_{(1, 16)}=0.099$, $p>0.5$). There was a significant difference for percentage of time spent in any particular quadrant for either treatment for most of the trials, most notably for CLAV.

Figure 10A:
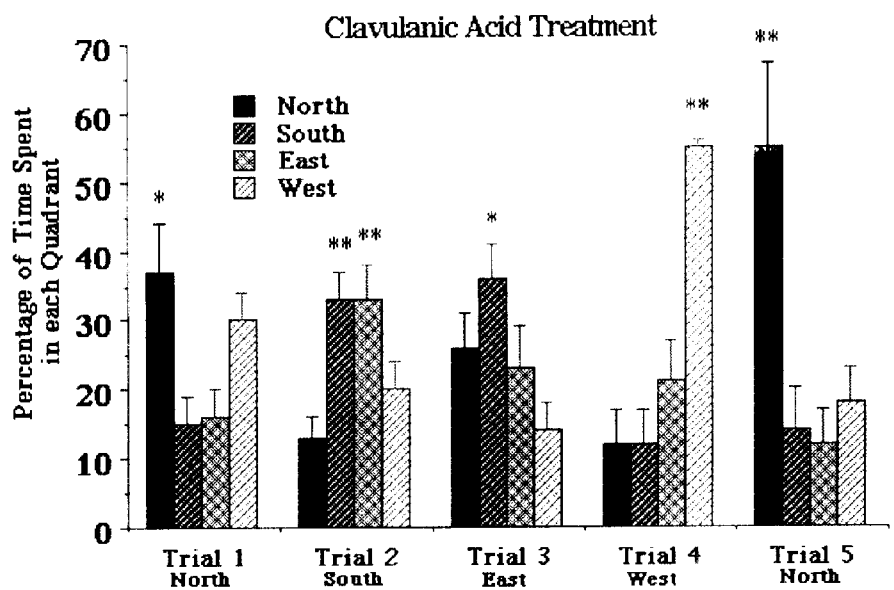
Figure 10B:
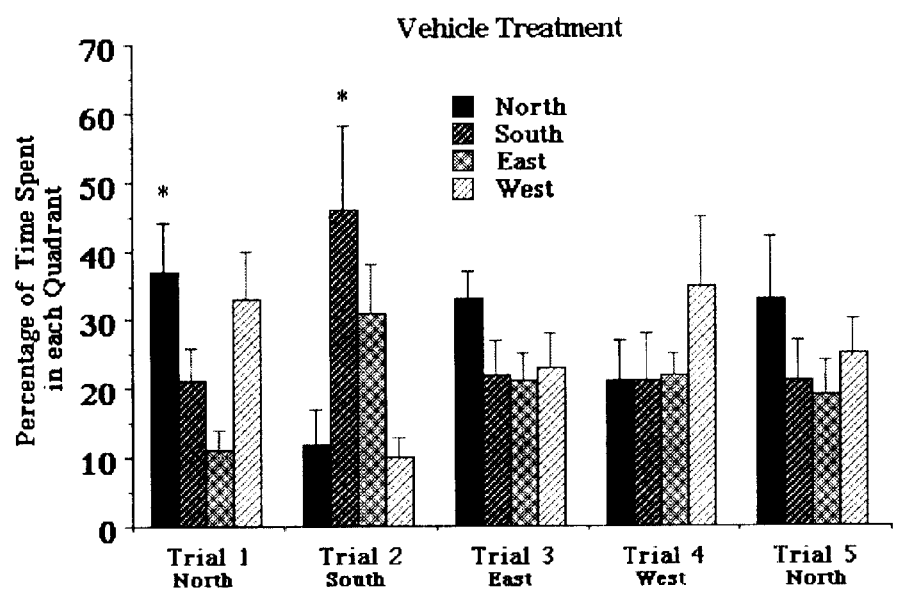
Figure 11:
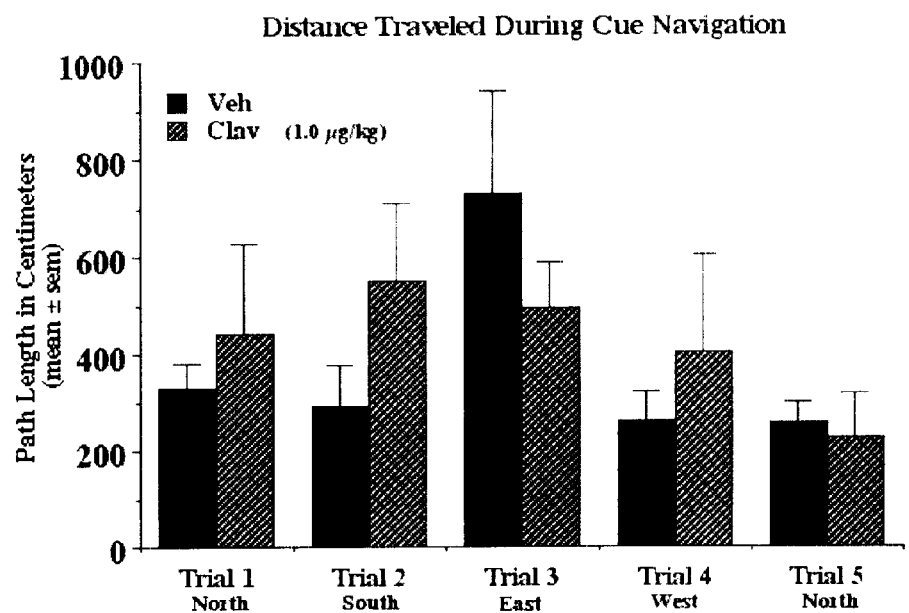
Figure 12:
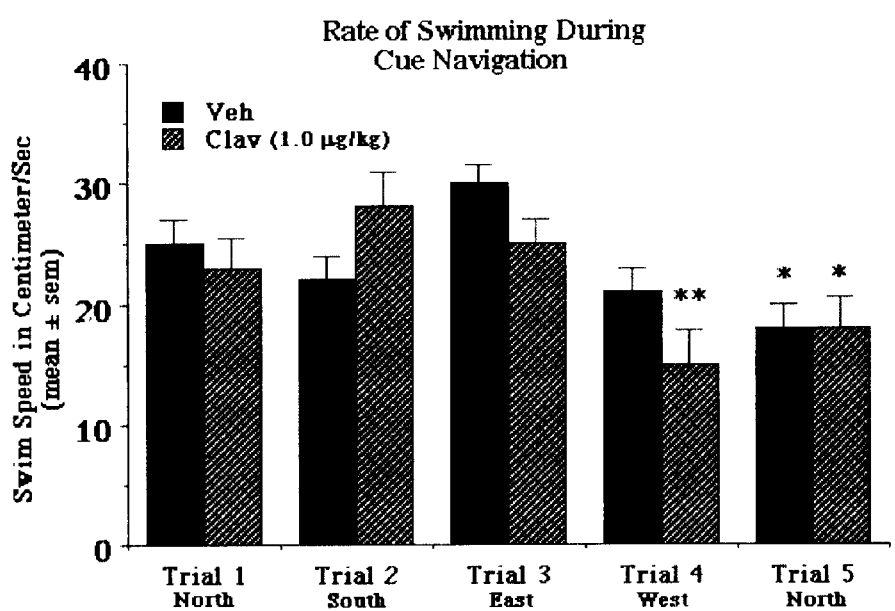

The distance traveled to find the platform was not significantly different between CLAV and vehicle animals ($F_{(1, 16)}=0.23$ $p>0.5$) (FIG. 11). While there was no significant main effect for treatment on swim rate ($F_{(1, 16)}=0.926$, $p>0.1$), there was a significant trails effect ($F_{(4, 64)}=7.87$, $p<0.001$) and interaction between factors ($F_{(4, 64)}=2.56$, $p<0.05$). Both treatments, but particularly CLAV showed reduced swim rates by Trial 4 ($p<0.01$) and Trial 5 ($p<0.05$). This probably reflects the fact that they knew where to look for the platform as shown in FIGS. 10A & B.

Summary

Clavulanic acid treated animals do not show any loss in learning and memory when tested for spatial and cue navigation in the Morris water maze. Indeed, on distance traveled to the hidden platform and percentage of time spent in the correct quadrant for both spatial and cue navigation, CLAV treated animals showed better performance than vehicle. These data show that the anxiolytic profile of CLAV is not accompanied by any disruption in learning and memory as is the case with benzodiazepine anxiolytics.

STUDIES ON MECHANISMS OF ACTION

VI. Clavulanic Acid and the Stress Response

Rationale

The ability of CLAV to reduce anxiety in stressful situations, i.e. the food deprivation and novel environment in the seed finding assay, and exposure to light and a novel environment in the elevated plus-maze, without altering motor activity or cognitive function is a significant finding. The potential of CLAV as an anxiolytic and therapeutic in the treatment of numerous affective disorders could be broadened if we had a clearer understanding of its mechanism of action. For example, could CLAV be altering anxiety by suppressing the natural stress response? The commonly prescribed benzodiazepine anxiolytics block both the normal circadian release and stress-mediated release of the hormone cortisol (Gram and Christensen, 1986; Petraglia et al., 1986; Hommer et al., 1986).

Experimental Protocol

The simple procedure of placing an adult male hamster into a novel environment for 5 min causes a significant, predictable increase in blood levels of cortisol (Weinberg and Wong 1986). This novelty test was used to assess the effects of CLAV on stress-induced release of cortisol. Two groups of male hamsters were treated IP with either CLAV (10 μg/kg, n=6), or saline vehicle (n=4). A third group (n=4) received no treatment or isolation stress and served as a control for basal levels of cortisol. Sixty min after treatment animals were taken from their home cage and placed into a novel cage for 5 min. Afterwards animals were sacrificed by decapitation and trunk blood collected for radioimmunoassay of cortisol. All animals were tested under reverse light-:dark conditions four hrs into the dark cycle. Data were compared with a one-way ANOVA followed by Fisher PLSD post hoc tests.

Results

There was a significant difference in the stress release of cortisol between treatments ($F_{(2, 11)}=10.03$ $p<0.01$). Vehicle ($p<0.05$) and CLAV ($p<0.01$) showed more than twice the blood level of cortisol as compared to the untreated, non-stressed control (FIG. 13).

Summary

The data show that the beta-lactam anxiolytic CLAV has no ostensible effect on the release of cortisol in response to the mild stress of exposure to a novel environment. This detail, combined with the absence of motor depression and cognitive impairment makes CLAV unique amongst the anxiolytics and suggests a highly specific, novel mechanism of action. At first glance one might think it would be advantageous to suppress the stress response. Indeed, hypercortisolism has been implicated in the pathophysiology of depression (Sacher et al., 1973). Chronic psychosocial stress leading to dysfunctional, hyperactive adrenal glands can be life threatening. However, a responsive hypothalamic-pituitary-adrenal axis is critical for normal physiology and behavior. Stressors that would normally help animals adapt to the environment can be fatal without the appropriate release of cortisol.

VII. Territorial or Offensive Aggression

Rationale

Continuing to study the CNS activity of CLAV in more complex behavioral models may help to clarify its mechanism(s) of action. For example, antagonistic, social interactions between animals require risk assessment, communicative and agonistic behaviors to settle disputes over territory, mates, food, etc. The neurotransmitters serotonin and vasopressin are fundamental in the CNS organization and expression of these behaviors in animals and humans (Ferris et al., 1997; Coccaro et al., 1998; Ferris 2000). To this end, CLAV was tested for effects on territorial or offensive aggression, i.e. defense of the home burrow against intruders.

Agonistic behavior can be classified as either offensive or defensive aggression (Blanchard and Blanchard, 1977; Adams, 19798; Albert and Walsh, 1984). Offensive aggression is characterized by an aggressor initiating an attack on an opponent; while, defensive aggression lacks active approach. Both types of aggression have their own unique neurobehavioral systems. The stimuli that elicit offensive and defense attack are different, as are the sequences of behaviors that accompany each agonistic response. While much of the empirical data supporting the notion of unique offensive and defensive neural networks have been collected from animal models, there are interesting and compelling similarities in human aggression that suggest a similar neural organization (Blanchard, 1984). Offensive aggression is easily studied using male golden hamsters tested in a resident/intruder paradigm, an established model of offensive aggression (Ferris and Potegal 1988) in the context of defending the home burrow. Placing an unfamiliar male hamster into the home cage of another male hamster elicits a well-defined sequence of agonistic behaviors from the resident that includes offensive aggression.

Experimental Protocol

Hamsters are nocturnal and as such all behavioral tests were performed during the first four hrs of the dark phase under dim red illumination. The resident was scored for offensive aggression, e.g., latency to bite the intruder, the total number of bites, total contact time with the intruder and flank marking over a 10 min test period (Ferris and Potegal, 1988). Flank marking is a form of olfactory communication in which a hamsters arches its back and rubs pheromone producing flank glands against objects in the environment (Johnston, 1986). Flank marking frequency is greatly enhanced during aggressive encounters and is particularly robust in dominant animals initiating and winning fights (Ferris et al., 1987).

Five male golden hamsters (130–140 g) were given IP injections of CLAV (200 μg/kg) and saline vehicle in a volume of ca. 0.2 ml. In pilot studies, it was discovered CLAV given IP at 1.0 μg/kg had no effect on aggressive behavior. Hence, it was necessary to test CLAV at a higher concentration but in a dose range that was still acceptable for pharmaceutical studies on aggressive behavior. Vehicle and CLAV treatments were counter balanced and randomized so all five animals received each treatment separated by at least 48 hrs. Animals were tested 90 min after treatment over a 10 min observation period. Latencies and contact time were analyzed with a two-way ANOVA. Non-parametric data, i.e., number of bites and flank marks were analyzed by Wilcoxon matched-pairs signed-ranks test.

Results

Figure 14:
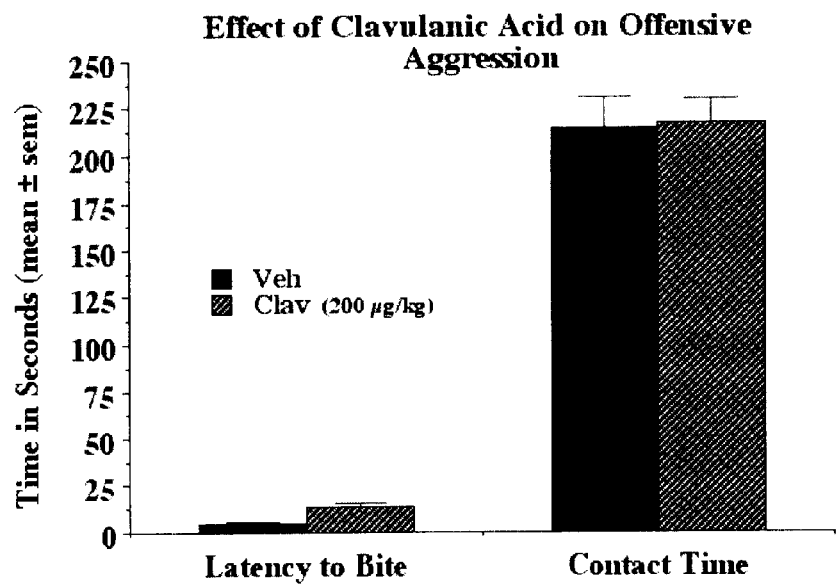

While there was no significant main effect for drug treatment ($F_{(1, 3)}$=7.40, $P<0.07$) for latency to bite the intruder there was a trend toward significance (FIG. 14). There was no significant main effect for drug treatment ($F_{(1, 3)}$=2.85, $p>0.1$) on contact time with the intruder (FIG. 14). There was a significant difference between drug treatments ($T=3.0$, $p<0.05$, $N=8$) and the number of bites on the intruder. CLAV treatment reduced the median number of bites to six as compared to thirteen for vehicle treated animals (FIG. 15). There was no significant effect of drug treatment ($T=4.0$, $p>0.1$, $N=5$) on the resident's flank marking behavior (FIG. 15).

Summary

Clavulanic acid has modest antiaggressive or serenic-like properties. Serenics are drugs used to treat impulsivity and violence (Olivier and Mos, 1991). Serenics should suppress offensive aggression without interfering with social, appetitive and cognitive behaviors. Social interest in an intruder, i.e. contact time was not altered by CLAV. Development of eltoprazine, one of the first serenics, was abandoned, in part, because it was found to increase fear and anxiety in animals (Olivier et al., 1994). The potent anxiolytic activity of CLAV excludes this possibility.

VIII. Interactions with Glutamyl Carboxypeptidase

CLAV has a very high binding affinity for the beta-lactamases. It is hypothesized that the presence of mammalian homologies to these bacterial enzymes and that these homologous proteins are involved in the regulation of neurotransmitter levels in the CNS. *E Coli* TEM beta lactamase has been cloned sequenced and crystilized to determine the active site motifs. The four putative binding sites on beta lactamase that could accommodate CLAV are designated active site I, II, III, and IV. These active sites, sequence location, and amino acid (AA) sequences are as follows:

Active site I:
35 AA's downstream from N-terminus: STTK (SEQ ID NO:1)

Active site II:
57 AA's downstream from STTK (SEQ ID NO: 1) motif: SGC, SGN, or SAN Active site III:
111 AA's downstream from SGC motif: KTG Active site IV:
41 AA's downstream from SGC motif: ENKD (SEQ ID NO:2)

Screening for amino acid sequence homologies between these beta-lactamase binding sites and mammalian enzymes, Revaax scientists identified an enzyme system in the brain that CLAV would potentially bind in a similar manner to beta-lactamase. The enzyme glutamyl carboxypeptidase (N-acetyl, alpha linked, acidic dipeptidase) or NAALADase (Pangalos et al, 1999) is responsible for regulating the glutamatergic neurotransmission pathways whose effects would be expressed in such behavioral outcomes as aggression, memory/cognition, and anxiety. As a result of the almost perfect overlap of the putative active sites of beta-lactamase and the conserved sequences in human and rat NAALADase, it was hypothesized that CLAV affects behavior by inhibiting NAALADase activity. The overlap sequence similarity between beta-lactamase and NAALA-Dase as shown below:

Clavulanic acid inhibits gram negative beta-lactamase enzymes in the range of 15–34 nM CLAV is effective at a dose of 10 ng/kg in the seed finding model of anxiety. If NAALADase were the human homologue to beta-lactamase then CLAV would be predicted to be a high affinity substrate.

IX. Seed Finding Following Blockade of NAALADase Activity

Rationale and Experimental Procedure

It was hypothesized that CLAV functioned as an anxiolytic in the seed finding assay by blocking NAALADase activity in the brain. If this notion were true then it would be predicted that drugs known to block NAALADase should also enhance seed finding. To this end, animals were treated with N-acetyl-beta-aspartyl-glutamic acid (beta-NAAG), a competitive inhibitor of NAALADase (Serval et al., 1992) and tested in the seed finding model of anxiety. The study was similar to that outlined in Section I with one notable exception. Since beta-NAAG does not readily cross the blood-brain barrier it had to be injected directly into the lateral ventricle where it could be carried by cerebrospinal fluid throughout the brain via the ventricular system. Beta-NAAG (FW 304) was given in a dose of 3 ng in a volume of 1 μl saline ICV. The average adult hamster brain weights ca. 1.2 g of which 22% is extracellular fluid. The estimated beta-NAAG concentration was 11 ng/ml or 36 nM.

Two groups of six animals each were fasted overnight as previously described and tested the following day. One group was treated with beta-NAAG and the other saline vehicle and one hr later timed for latency to find the hidden sunflower seeds. A Student t-test for unpaired data was used for statistical comparisons.

Results

Figure 16:
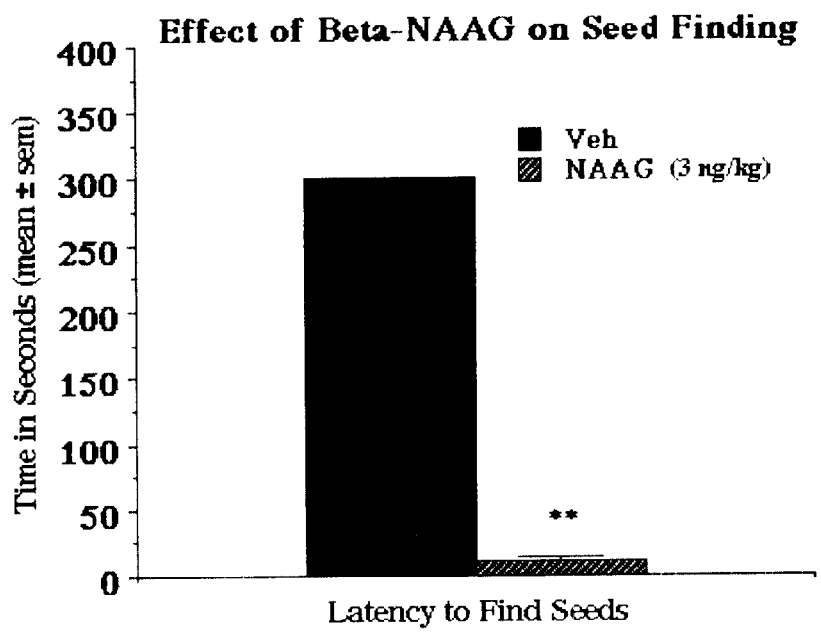

The difference in latency to find the seeds was significantly ($p<0.001$) different between treatments (FIG. 16). Indeed, the none of the six animals microinjected with saline vehicle found the seeds in the five min observation period. However, three days later when these same animals were microinjected with beta-NAAG (3 μg/μl) and tested for seed finding they showed a mean latency of 21.8±9.7 sec.

Summary

The data show that beta-NAAG a specific NAALADase inhibitor can dramatically reduced the latency to find hidden sunflower seeds, a biological activity shared by CLAV. Since beta-NAAG was active in the seed finding model of anxiety then the hypothesis that beta-NAAG and CLAV share a common mechanism of action is not rejected. From these data the hypothesis can be expanded to predict that beta-NAAG and CLAV show similar effects on a range of biological and behavioral measures. To this end, animals were tested for offensive aggression in the resident intruder paradigm as described in Section VII. As reported earlier, when given in high concentrations, CLAV has only a modest effect on offensive. While CLAV can enhance seed finding at a dose of 10 ng/kg it has only a modest effect on offensive aggression even with doses as high as 200 μg/kg. If beta-NAAG and CLAV share a common mechanism then beta-NAAG should have little or no effect on aggression.

X. Effect of NAALADase Blockade on Offensive Aggression

Experimental Procedure

The animals tested in this study were those used in Section IX. After the seed finding assay, beta-NAAG (n=6) and saline vehicle (n=6) treated animals remained in their home cage and were presented with a smaller, male intruder. The resident was scored for latency to bite, bites, contact time and flank marking over a 10 min observation period. Latency to bite and contact time between treatments were compared with Student t-tests. Non-parametric measures of bites and flank marks for beta-NAAG vs vehicle were compared with Mann-Whitney.

Results

Figure 17:
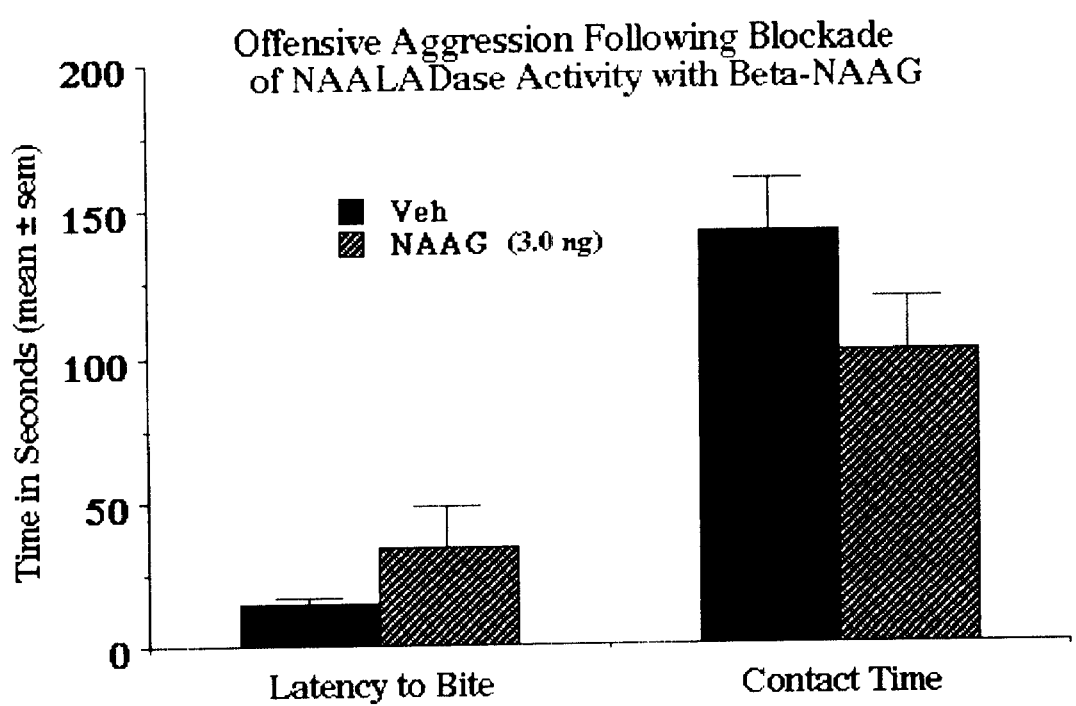
Figure 18:
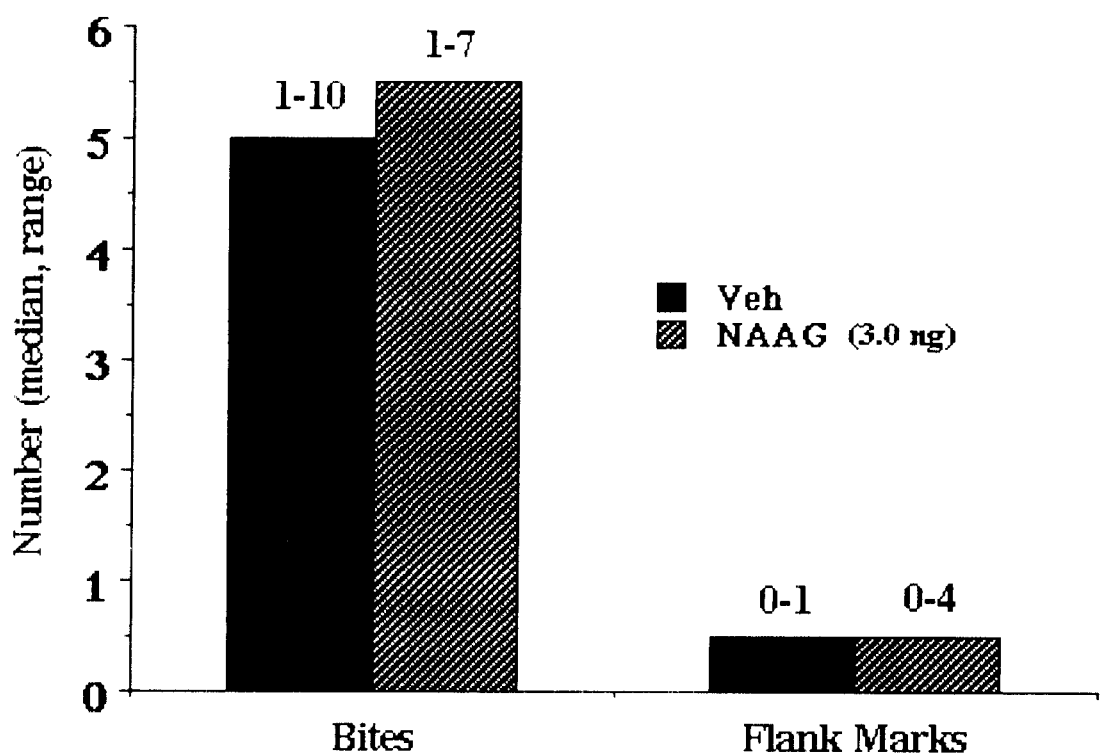

There were no significant differences between beta-NAAG and vehicle-treated animals for any measures of offensive aggression (FIGS. 17 & 18).

Summary

Blocking NAALADase activity with beta-NAAG does not alter offensive aggression as tested in the resident intruder paradigm. This finding is not inconsistent with the notion that CLAV and beta-NAAG share a common mechanism—blockade of NAALADase activity.

I claim:

1. A method of treatment of behavioral disorders in a patient in need of such treatment wherein the behavioral disorder is selected from aggressive disorder, obsessive-compulsive disorder, anxiety, depression or ADHD, said method comprising the step of administering a compound selected from the group consisting of clavulanic acid, pharmaceutically acceptable salts thereof, and active ester forms thereof hydrolyzable in vivo to clavulanic acid to said patient in an amount effective to modify patient behavior.

2. The method of claim 1 wherein the compound is administered as an antiaggressive agent to control impulsivity and violence in said patient, wherein said patient is afflicted with autism, Tourette's syndrome, mental retardation, psychosis, mania, or senile dementia or wherein said patient has a personality disorder and history of inappropriate aggression.

3. The method of claim 1 wherein the compound is administered to a human patient suffering a behavioral disorder comprising anxiety.

4. The method of claim 1 wherein the compound is administered to a human patient suffering a behavioral disorder comprising ADHD.

5. The method of claim 1 further comprising the step of administering an effective amount of a P-glycoprotein efflux pump inhibitor.

6. The method of claim 1 wherein the neurologically active compound is administered in combination with an effective amount of a P-glycoprotein efflux pump inhibitor.

7. A method of treating prostate disease selected from prostate cancer or benign prostatic hyperplasia in a human patient, said method comprising the step of administering to said patient a composition comprising a compound selected from the group consisting of clavulanic acid, pharmaceutically acceptable salts, and ester forms thereof, wherein said compound is administered in an amount effective to retard the progress of the disease or to reduce the symptoms of the disease.

8. A pharmaceutical formulation in unit dosage form for neurotherapeutic use comprising about 0.1 to about 10 mg of clavulanic acid or a pharmaceutically acceptable salt thereof and a pharmaceutically acceptable carrier, said formulation being free of clinically effective amounts of another β-lactam antibiotic.

9. The formulation of claim 8 in an oral dosage form.

10. The formulation of claim 8 in a parental dosage form.

11. The formulation of claim 8 in a prolonged release dosage form.

12. The formulation of claim 8 in a lozenge dosage form.

* * * * *

UNITED STATES PATENT AND TRADEMARK OFFICE
CERTIFICATE OF CORRECTION

PATENT NO. : 6,610,681 B1
DATED : August 26, 2003
INVENTOR(S) : Gary A. Koppel

It is certified that error appears in the above-identified patent and that said Letters Patent is hereby corrected as shown below:

Column 34,
Line 33, change "parental" to -- parenteral --.

Signed and Sealed this

Fourteenth Day of October, 2003

JAMES E. ROGAN
*Director of the United States Patent and Trademark Office*